United States Patent
Kolesnick et al.

(10) Patent No.: US 10,975,169 B1
(45) Date of Patent: Apr. 13, 2021

(54) METHODS FOR TREATING DIABETIC RETINOPATHY USING ANTI-CERAMIDE MONOCLONAL ANTIBODY 2A2

(71) Applicants: MEMORIAL SLOAN KETTERING CANCER CENTER, New York, NY (US); BOARD OF TRUSTEES OF MICHIGAN STATE UNIVERSITY, East Lansing, MI (US)

(72) Inventors: Richard Kolesnick, New York, NY (US); Julia Busik, East Lansing, MI (US)

(73) Assignees: MEMORIAL SLOAN KETTERING CANCER CENTER, New York, NY (US); BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 16/752,469

(22) Filed: Jan. 24, 2020

Related U.S. Application Data

(60) Provisional application No. 62/907,287, filed on Sep. 27, 2019.

(51) Int. Cl.
| | | |
|---|---|---|
| C07K 16/44 | (2006.01) | |
| A61K 9/00 | (2006.01) | |
| A61P 27/02 | (2006.01) | |
| A61K 39/00 | (2006.01) | |

(52) U.S. Cl.
CPC ............ *C07K 16/44* (2013.01); *A61K 9/0019* (2013.01); *A61K 9/0048* (2013.01); *A61P 27/02* (2018.01); *A61K 2039/505* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,091,513 A | 2/1992 | Huston et al. | |
| 5,132,405 A | 7/1992 | Huston et al. | |
| 8,562,993 B2 | 10/2013 | Rotolo et al. | |
| 10,124,008 B2 | 11/2018 | Lakkaraju et al. | |
| 10,450,385 B2 | 10/2019 | Rotolo et al. | |
| 2016/0032009 A1* | 2/2016 | Cheung .............. | A61K 51/1045 424/135.1 |

FOREIGN PATENT DOCUMENTS

| | | |
|---|---|---|
| WO | WO-93/11161 A1 | 6/1993 |
| WO | WO-94/13804 A1 | 6/1994 |
| WO | WO-2006/079372 A1 | 8/2006 |

OTHER PUBLICATIONS

Beckmann et al., "Inhibition of acid sphingomyelinase by tricyclic antidepressants and analogons", Frontiers in Physiology, Membrane Physiology and Membrane Biophysics, vol. 5, Article 331, Sep. 2, 2014, pp. 1-14.

Bressler et al., "Change in Diabetic Retinopathy Through 2 Years: Secondary Analysis of a Randomized Clinical Trial Comparing Aflibercept, Bevacizumab, and Ranibizumab", JAMA Ophthalmology, vol. 135, No. 6, Jun. 2017 (published online Apr. 27, 2017), pp. 558-568, including supplementary content (33 pages).

Busik et al., "Diabetic retinopathy is associated with bone marrow neuropathy and a depressed peripheral clock", The Journal of Experimental Medicine, vol. 206, No. 13, Dec. 21, 2009, pp. 2897-2906.

Busik et al., "Examining the role of lipid mediators in diabetic retinopathy", Clinical Lipidology, vol. 7, No. 6, 2012, pp. 661-675.

Chakravarthy et al., "Imbalances in Mobilization and Activation of Pro-Inflammatory and Vascular Reparative Bone Marrow-Derived Cells in Diabetic Retinopathy", PLoS One, vol. 11, No. 1, e0146829, Jan. 13, 2016, pp. 1-21.

Chakravarthy et al., "Role of Acid Sphingomyelinase in Shifting the Balance Between Proinflammatory and Reparative Bone Marrow Cells in Diabetic Retinopathy", Stem Cells, vol. 34 (4), Dec. 16, 2015, pp. 972-983 (15 pages).

Chen et al., "Anti-inflammatory Effect of Docosahexaenoic Acid on Cytokine-Induced Adhesion Molecule Expression in Human Retinal Vascular Endothelial Cells", Investigative Ophthalmology & Visual Science, vol. 46 No. 11, Nov. 2005, pp. 4342-4347.

Chen et al., "Inhibition of Cytokine Signaling in Human Retinal Endothelial Cells through Modification of Caveolae/Lipid Rafts by Docosahexaenoic Acid", Investigative Ophthalmology & Visual Science, vol. 48, No. 1, Jan. 2007, pp. 18-26.

Elman et al., "Randomized Trial Evaluating Ranibizumab Plus Prompt or Deferred Laser or Triamcinolone Plus Prompt Laser for Diabetic Macular Edema", The Diabetic Retinopathy Clinical Research Network, Ophthalmology, vol. 117, No. 6, pp. 1064-1077.e35, (49 pages).

Kielczewski et al., "Insulin-like Growth Factor Binding Protein-3 Mediates Vascular Repair by Enhancing Nitric Oxide Generation", Circulation Research, vol. 105, No. 9, Oct. 23, 2009, pp. 897-905.

Martinez-Zapata et al., "Anti-vascular endothelial growth factor for proliferative diabetic retinopathy", Cochrane Database of Systemic Reviews, Issue 11, Art. No. CD008721, 2014, pp. 1-68 (70 pages).

Nguyen et al., "Ranibizumab for Diabetic Macular Edema: Results from 2 Phase III Randomized Trials: Rise and Ride", Ophthalmology, vol. 119, No. 4, Apr. 2012, pp. 789-801.

Opreanu et al., "Inhibition of Cytokine Signaling in Human Retinal Endothelial Cells through Downregulation of Sphingomyelinases by Docosahexaenoic Acid", Investigative Ophthalmology & Visual Science, vol. 51, No. 6, Jun. 2010, pp. 3253-3263.

(Continued)

*Primary Examiner* — Sharon X Wen
(74) *Attorney, Agent, or Firm* — Foley & Lardner LLP

(57) ABSTRACT

The present disclosure provides methods of treating diabetic retinopathy and ocular inflammatory diseases with anti-ceramide antibodies and antibody fragments.

19 Claims, 7 Drawing Sheets
Specification includes a Sequence Listing.

(56) References Cited

OTHER PUBLICATIONS

Opreanu et al., "The Unconventional Role of Acid Sphingomyelinase in Regulation of Retinal Microangiopathy in Diabetic Human and Animal Models", Diabetes, vol. 60, No. 9, Sep. 2011, 2370-2378, including supplementary data.
Sun et al., "Rationale and Application of the Protocol S Anti-Vascular Endothelial Growth Factor Algorithm for Proliferative Diabetic Retinopathy", Ophthalmology, vol. 126, No. 1, Jan. 2019, pp. 87-95.
Tikhonenko et al., "N-3 Polyunsaturated Fatty Acids Prevent Diabetic Retinopathy by Inhibition of Retinal Vascular Damage and Enhanced Endothelial Progenitor Cell Reparative Function", PLoS One, vol. 8, Issue 1, e55177, Jan. 29, 2013, pp. 1-10.
Tikhonenko et al., "Remodeling of Retinal Fatty Acids in an Animal Model of Diabetes: A Decrease in Long-Chain Polyunsaturated Fatty Acids is Associated With a Decrease in Fatty Acid Elongases Elovl2 and Elovl4", Diabetes, vol. 59, No. 1, Jan. 2010, pp. 219-227.

\* cited by examiner

SEQUENCE LISTING

```
<160> NUMBER OF SEQ ID NOS: 42

<210> SEQ ID NO 1
<211> LENGTH: 10
<212> TYPE: PRT
<213> ORGANISM: Mus musculus

<400> SEQUENCE: 1

Gly Tyr Thr Phe Thr Asp His Thr Ile His
1               5                   10

<210> SEQ ID NO 2
<211> LENGTH: 17
<212> TYPE: PRT
<213> ORGANISM: Mus musculus

<400> SEQUENCE: 2

Tyr Asn Tyr Pro Arg Asp Gly Ser Thr Lys Tyr Asn Glu Lys Phe Lys
1               5                   10                  15

Gly

<210> SEQ ID NO 3
<211> LENGTH: 11
<212> TYPE: PRT
<213> ORGANISM: Mus musculus
```

```
<400> SEQUENCE: 3

Gly Phe Ile Thr Thr Val Val Pro Ser Ala Tyr
1               5                   10

<210> SEQ ID NO 4
<211> LENGTH: 11
<212> TYPE: PRT
<213> ORGANISM: Mus musculus

<400> SEQUENCE: 4

Arg Ala Ser Lys Ser Ile Ser Lys Tyr Leu Ala
1               5                   10

<210> SEQ ID NO 5
<211> LENGTH: 7
<212> TYPE: PRT
<213> ORGANISM: Mus musculus

<400> SEQUENCE: 5

Ser Gly Ser Thr Leu Gln Ser
1               5

<210> SEQ ID NO 6
<211> LENGTH: 9
<212> TYPE: PRT
<213> ORGANISM: Mus musculus

<400> SEQUENCE: 6

Gln Gln His Asn Glu Tyr Pro Trp Thr
1               5

<210> SEQ ID NO 7
<211> LENGTH: 119
<212> TYPE: PRT
<213> ORGANISM: Mus musculus

<400> SEQUENCE: 7

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
                20                  25                  30

Thr Ile His Trp Met Lys Gln Arg Pro Glu Gln Gly Leu Glu Trp Ile
            35                  40                  45

Gly Tyr Asn Pro Arg Asp Gly Ser Thr Lys Tyr Asn Glu Lys Phe Gly
        50                  55                  60

Lys Ala Thr Leu Thr Asp Ala Asp Lys Ser Ser Ser Thr Ala Tyr Met
65                  70                  75                  80

Gln Leu Asn Ser Leu Thr Ser Glu Asp Ser Ala Val Tyr Phe Cys Ala
                85                  90                  95

Lys Gly Phe Ile Thr Thr Val Val Pro Ser Ala Tyr Trp Gly Gln Gly
            100                 105                 110

Thr Leu Val Thr Val Ser Ala
        115

<210> SEQ ID NO 8
<211> LENGTH: 107
<212> TYPE: PRT
<213> ORGANISM: Mus musculus

<400> SEQUENCE: 8

Asp Val Gln Ile Thr Gln Ser Pro Ser Tyr Leu Ala Ala Ser Pro Gly
```

```
            1               5                  10                 15
        Glu Thr Ile Thr Ile Asn Cys Arg Ala Ser Lys Ser Ile Ser Lys Tyr
                        20                 25                 30
        Leu Ala Trp Tyr Gln Glu Lys Pro Gly Lys Thr Asn Lys Leu Leu Ile
                        35                 40                 45
        Tyr Ser Gly Ser Thr Leu Gln Ser Gly Ile Pro Ser Arg Phe Ser Gly
                        50                 55                 60
        Ser Gly Ser Gly Thr Asp Phe Thr Leu Thr Ile Ser Ser Leu Glu Pro
        65                  70                 75                 80
        Glu Asp Phe Ala Met Tyr Tyr Cys Gln Gln His Asn Glu Tyr Pro Trp
                        85                 90                 95
        Thr Phe Gly Gly Gly Thr Lys Leu Glu Ile Lys
                        100                105
```

<210> SEQ ID NO 9
<211> LENGTH: 10
<212> TYPE: PRT
<213> ORGANISM: Mus musculus

<400> SEQUENCE: 9

```
Gly Tyr Ala Phe Ser Ser Tyr Trp Met Asn
1               5                  10
```

<210> SEQ ID NO 10
<211> LENGTH: 17
<212> TYPE: PRT
<213> ORGANISM: Mus musculus

<400> SEQUENCE: 10

```
Gln Ile Tyr Pro Gly Asp Gly Asp Thr Asn Tyr Asn Gly Lys Phe Lys
1               5                  10                 15
Gly
```

<210> SEQ ID NO 11
<211> LENGTH: 10
<212> TYPE: PRT
<213> ORGANISM: Mus musculus

<400> SEQUENCE: 11

```
Arg Cys Tyr Tyr Gly Leu Tyr Phe Asp Val
1               5                  10
```

<210> SEQ ID NO 12
<211> LENGTH: 11
<212> TYPE: PRT
<213> ORGANISM: Mus musculus

<400> SEQUENCE: 12

```
Lys Ala Ser Gln Asp Ile Asn Arg Tyr Leu Ser
1               5                  10
```

<210> SEQ ID NO 13
<211> LENGTH: 7
<212> TYPE: PRT
<213> ORGANISM: Mus musculus

<400> SEQUENCE: 13

```
Arg Ala Asn Arg Leu Val Asp
1               5
```

<210> SEQ ID NO 14

```
<211> LENGTH: 9
<212> TYPE: PRT
<213> ORGANISM: Mus musculus

<400> SEQUENCE: 14

Leu Gln Tyr Asp Glu Phe Pro Tyr Thr
1               5

<210> SEQ ID NO 15
<211> LENGTH: 119
<212> TYPE: PRT
<213> ORGANISM: Mus musculus

<400> SEQUENCE: 15

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Lys Gly Leu Glu Trp Ile
            35                  40                  45

Gly Gln Ile Tyr Pro Gly Asp Gly Asp Thr Asn Tyr Asn Gly Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Arg Cys Tyr Tyr Gly Leu Tyr Phe Asp Val Trp Gly Thr Gly
                100                 105                 110

Thr Thr Val Thr Val Ser Ser
        115

<210> SEQ ID NO 16
<211> LENGTH: 108
<212> TYPE: PRT
<213> ORGANISM: Mus musculus

<400> SEQUENCE: 16

Asp Ile Lys Met Thr Gln Ser Pro Ser Ser Arg Tyr Ala Ser Leu Gly
1               5                   10                  15

Glu Arg Val Thr Ile Thr Cys Lys Ala Ser Gln Asp Ile Asn Arg Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser
        50                  55                  60

Gly Ser Gly Ser Gly Gln Asp Tyr Ser Leu Thr Ile Ser Ser Leu Glu
65                  70                  75                  80

Tyr Glu Asp Met Gly Ile Tyr Tyr Cys Leu Gln Tyr Asp Glu Phe Pro
                85                  90                  95

Tyr Thr Phe Gly Gly Gly Thr Lys Leu Glu Ile Lys
                100                 105

<210> SEQ ID NO 17
<211> LENGTH: 10
<212> TYPE: PRT
<213> ORGANISM: Mus musculus

<400> SEQUENCE: 17

Gly Tyr Thr Phe Thr Ser Tyr Trp Met His
```

```
1               5                    10
```

<210> SEQ ID NO 18
<211> LENGTH: 16
<212> TYPE: PRT
<213> ORGANISM: Mus musculus

<400> SEQUENCE: 18

```
Tyr Ile Asn Pro Ser Gly Tyr Thr Lys Tyr Asn Gln Phe Lys Asp
1               5                   10                  15
```

<210> SEQ ID NO 19
<211> LENGTH: 8
<212> TYPE: PRT
<213> ORGANISM: Mus musculus

<400> SEQUENCE: 19

```
Gly Gly Tyr Tyr Gly Phe Ala Tyr
1               5
```

<210> SEQ ID NO 20
<211> LENGTH: 10
<212> TYPE: PRT
<213> ORGANISM: Mus musculus

<400> SEQUENCE: 20

```
Ser Ala Ser Ser Ser Val Ser Tyr Met Tyr
1               5                   10
```

<210> SEQ ID NO 21
<211> LENGTH: 7
<212> TYPE: PRT
<213> ORGANISM: Mus musculus

<400> SEQUENCE: 21

```
Leu Thr Ser Asn Leu Ala Ser
1               5
```

<210> SEQ ID NO 22
<211> LENGTH: 9
<212> TYPE: PRT
<213> ORGANISM: Mus musculus

<400> SEQUENCE: 22

```
Gln Gln Trp Ser Ser Asn Pro Leu Thr
1               5
```

<210> SEQ ID NO 23
<211> LENGTH: 117
<212> TYPE: PRT
<213> ORGANISM: Mus musculus

<400> SEQUENCE: 23

```
Gln Val Gln Leu Gln Gln Ser Gly Ala Glu Leu Ala Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Tyr Ile Asn Pro Ser Ser Gly Tyr Thr Lys Tyr Asn Gln Lys Phe
        50                  55                  60

Lys Asp Lys Ala Thr Leu Thr Ala Asp Lys Ser Ser Ser Thr Ala Tyr
65                  70                  75                  80
```

```
Met Gln Leu Ser Ser Leu Thr Tyr Glu Asp Ser Ala Val Tyr Cys
                85                  90                  95

Ala Arg Gly Gly Tyr Tyr Gly Phe Ala Tyr Trp Gly Gln Gly Thr Leu
            100                 105                 110

Val Thr Val Ser Ala
        115

<210> SEQ ID NO 24
<211> LENGTH: 106
<212> TYPE: PRT
<213> ORGANISM: Mus musculus

<400> SEQUENCE: 24

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 25
<211> LENGTH: 10
<212> TYPE: PRT
<213> ORGANISM: Mus musculus

<400> SEQUENCE: 25

Gly Phe Ser Leu Thr Gly Tyr Gly Val His
1               5                   10

<210> SEQ ID NO 26
<211> LENGTH: 16
<212> TYPE: PRT
<213> ORGANISM: Mus musculus

<400> SEQUENCE: 26

Val Ile Trp Ser Gly Gly Ser Thr Asp Tyr Asn Ala Ala Phe Ile Ser
1               5                   10                  15

<210> SEQ ID NO 27
<211> LENGTH: 10
<212> TYPE: PRT
<213> ORGANISM: Mus musculus

<400> SEQUENCE: 27

Asn Tyr Gly Tyr Asp Tyr Ala Met Asp Tyr
1               5                   10

<210> SEQ ID NO 28
<211> LENGTH: 11
<212> TYPE: PRT
<213> ORGANISM: Mus musculus

<400> SEQUENCE: 28
```

-continued

Arg Ala Ser Gln Ser Ile Gly Thr Ser Ile His
1               5                   10

<210> SEQ ID NO 29
<211> LENGTH: 7
<212> TYPE: PRT
<213> ORGANISM: Mus musculus

<400> SEQUENCE: 29

Tyr Ala Ser Glu Ser Ile Ser
1               5

<210> SEQ ID NO 30
<211> LENGTH: 9
<212> TYPE: PRT
<213> ORGANISM: Mus musculus

<400> SEQUENCE: 30

Gln Gln Ser Asn Ser Trp Pro Phe Thr
1               5

<210> SEQ ID NO 31
<211> LENGTH: 116
<212> TYPE: PRT
<213> ORGANISM: Mus musculus

<400> SEQUENCE: 31

Gln Val Gln Leu Lys Gln Ser Gly Pro Gly Val Gln Pro Ser Ser Leu
1               5                   10                  15

Ser Ile Thr Cys Thr Val Ser Gly Phe Ser Leu Thr Ser Tyr Gly Val
                20                  25                  30

His Trp Val Arg Gln Ser Pro Gly Lys Gly Leu Glu Trp Leu Gly Val
            35                  40                  45

Ile Trp Ser Gly Gly Ser Thr Asp Tyr Asn Ala Ala Phe Ile Ser Arg
        50                  55                  60

Leu Ser Ile Ser Lys Asp Asn Ser Lys Ser Gln Val Phe Phe Lys Met
65                  70                  75                  80

Asn Ser Leu Gln Ala Asp Asp Thr Ala Ile Tyr Tyr Cys Ala Arg Asn
                85                  90                  95

Tyr Gly Tyr Asp Tyr Ala Met Asp Tyr Trp Gly Gln Gly Thr Ser Val
            100                 105                 110

Thr Val Ser Ser
        115

<210> SEQ ID NO 32
<211> LENGTH: 107
<212> TYPE: PRT
<213> ORGANISM: Mus musculus

<400> SEQUENCE: 32

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser

```
            65                  70                  75                  80
Glu Asp Ile Ala Asp Tyr Tyr Cys Gln Gln Ser Asn Ser Trp Pro Phe
                    85                  90                  95

Thr Phe Gly Ser Gly Thr Lys Leu Glu Ile Lys
            100                 105
```

<210> SEQ ID NO 33
<211> LENGTH: 5
<212> TYPE: PRT
<213> ORGANISM: Mus musculus

<400> SEQUENCE: 33

```
Asn Tyr Trp Met His
1               5
```

<210> SEQ ID NO 34
<211> LENGTH: 17
<212> TYPE: PRT
<213> ORGANISM: Mus musculus

<400> SEQUENCE: 34

```
Ala Ile Tyr Pro Gly Asp Ser Asp Thr Ser Tyr Asn Gln Lys Phe Lys
1               5                   10                  15
Gly
```

<210> SEQ ID NO 35
<211> LENGTH: 6
<212> TYPE: PRT
<213> ORGANISM: Mus musculus

<400> SEQUENCE: 35

```
Leu Tyr Tyr Gly Tyr Asp
1               5
```

<210> SEQ ID NO 36
<211> LENGTH: 16
<212> TYPE: PRT
<213> ORGANISM: Mus musculus

<400> SEQUENCE: 36

```
Lys Ser Ser Gln Ser Leu Ile Asp Ser Asp Gly Lys Thr Phe Leu Asn
1               5                   10                  15
```

<210> SEQ ID NO 37
<211> LENGTH: 7
<212> TYPE: PRT
<213> ORGANISM: Mus musculus

<400> SEQUENCE: 37

```
Leu Val Ser Lys Leu Asp Ser
1               5
```

<210> SEQ ID NO 38
<211> LENGTH: 9
<212> TYPE: PRT
<213> ORGANISM: Mus musculus

<400> SEQUENCE: 38

```
Trp Gln Gly Thr His Phe Pro Tyr Thr
1               5
```

<210> SEQ ID NO 39
<211> LENGTH: 115

```
<212> TYPE: PRT
<213> ORGANISM: Mus musculus

<400> SEQUENCE: 39

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Asn Tyr
                20                  25                  30

Trp Met His Trp Val Lys Gln Arg Pro Val Gln Gly Leu Glu Trp Ile
            35                  40                  45

Gly Ala Ile Tyr Pro Gly Asp Ser Asp Thr Ser Tyr Asn Gln Lys Phe
        50                  55                  60

Lys Gly Lys Ala Lys Leu Thr Ala Val Thr Ser Thr Ser Thr Ala Phe
65                  70                  75                  80

Met Glu Leu Ser Ser Leu Thr Asn Glu Asp Ser Ala Val Tyr Tyr Cys
                85                  90                  95

Thr Gly Leu Tyr Tyr Gly Tyr Asp Trp Gly Gln Gly Thr Thr Leu Thr
            100                 105                 110

Val Ser Ser
        115

<210> SEQ ID NO 40
<211> LENGTH: 112
<212> TYPE: PRT
<213> ORGANISM: Mus musculus

<400> SEQUENCE: 40

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Ile Asp Ser
                20                  25                  30

Asp Gly Lys Thr Phe Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Leu Tyr Tyr Cys Trp Gln Gly
                85                  90                  95

Thr His Phe Pro Tyr Thr Phe Gly Gly Gly Thr Lys Leu Glu Ile Lys
            100                 105                 110

<210> SEQ ID NO 41
<211> LENGTH: 463
<212> TYPE: PRT
<213> ORGANISM: Homo sapiens

<400> SEQUENCE: 41

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asn Tyr Trp Met His Trp Val Arg Gln Ala Pro Gly Gln Gly Leu
        50                  55                  60

Glu Trp Met Gly Ala Ile Tyr Pro Gly Asp Ser Asp Thr Ser Tyr Asn
```

```
                65                  70                  75                  80
        Gln Lys Phe Lys Gly Arg Val Thr Met Thr Arg Asp Thr Ser Thr Ser
                            85                  90                  95

Thr Val Tyr Met Glu Leu Ser Ser Leu Arg Ser Glu Asp Thr Ala Val
                        100                 105                 110

Tyr Tyr Cys Ala Arg Leu Tyr Gly Tyr Asp Trp Gly Gln Gly Thr
                    115                 120                 125

Thr Val Thr Val Ser Ser Ala Ser Thr Lys Gly Pro Ser Val Phe Pro
                130                 135                 140

Leu Ala Pro Ser Ser Lys Ser Thr Ser Gly Gly Thr Ala Ala Leu Gly
        145                 150                 155                 160

Cys Leu Val Lys Asp Tyr Phe Pro Glu Pro Val Thr Val Ser Trp Asn
                        165                 170                 175

Ser Gly Ala Leu Thr Ser Gly Val His Thr Phe Pro Ala Val Leu Gln
                    180                 185                 190

Ser Ser Gly Leu Tyr Ser Leu Ser Ser Val Val Thr Val Pro Ser Ser
                195                 200                 205

Ser Leu Gly Thr Gln Thr Tyr Ile Cys Asn Val Asn His Lys Pro Ser
        210                 215                 220

Asn Thr Lys Val Asp Lys Lys Val Glu Pro Lys Ser Cys Asp Lys Thr
        225                 230                 235                 240

His Thr Cys Pro Pro Cys Pro Ala Pro Glu Leu Leu Gly Gly Pro Ser
                        245                 250                 255

Val Phe Leu Phe Pro Pro Lys Pro Lys Asp Thr Leu Met Ile Ser Arg
                    260                 265                 270

Thr Pro Glu Val Thr Cys Val Val Val Asp Val Ser His Glu Asp Pro
                275                 280                 285

Glu Val Lys Phe Asn Trp Tyr Val Asp Gly Val Glu Val His Asn Ala
                    290                 295                 300

Lys Thr Lys Pro Arg Glu Glu Gln Tyr Asn Ser Thr Tyr Arg Val Val
        305                 310                 315                 320

Ser Val Leu Thr Val Leu His Gln Asp Trp Leu Asn Gly Lys Glu Tyr
                        325                 330                 335

Lys Cys Lys Val Ser Asn Lys Ala Leu Pro Ala Pro Ile Glu Lys Thr
                    340                 345                 350

Ile Ser Lys Ala Lys Gly Gln Pro Arg Glu Pro Gln Val Tyr Thr Leu
                355                 360                 365

Pro Pro Ser Arg Asp Glu Leu Thr Lys Asn Gln Val Ser Leu Thr Cys
        370                 375                 380

Leu Val Lys Gly Phe Tyr Pro Ser Asp Ile Ala Val Glu Trp Glu Ser
        385                 390                 395                 400

Asn Gly Gln Pro Glu Asn Asn Tyr Lys Thr Thr Pro Pro Val Leu Asp
                        405                 410                 415

Ser Asp Gly Ser Phe Phe Leu Tyr Ser Lys Leu Thr Val Asp Lys Ser
                    420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly
                450                 455                 460

<210> SEQ ID NO 42
<211> LENGTH: 239
<212> TYPE: PRT
<213> ORGANISM: Homo sapiens
```

```
<400> SEQUENCE: 42

Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
                20                  25                  30

Val Thr Leu Gly Gln Pro Ala Ser Ile Ser Cys Lys Ser Ser Gln Ser
            35                  40                  45

Leu Ile Asp Ser Asp Gly Lys Thr Phe Leu Asn Trp Phe Gln Gln Arg
        50                  55                  60

Pro Gly Gln Ser Pro Arg Arg Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Gly Thr His Phe Pro Tyr Thr Phe Gly Gln Gly Thr Lys
        115                 120                 125

Leu Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

US 10,975,169 B1

METHODS FOR TREATING DIABETIC RETINOPATHY USING ANTI-CERAMIDE MONOCLONAL ANTIBODY 2A2

CROSS-REFERENCE TO RELATED APPLICATIONS

This application claims priority to U.S. Provisional Application No. 62/907,287, filed Sep. 27, 2019, the content of which is incorporated herein by reference in its entirety.

STATEMENT OF GOVERNMENT SUPPORT

This invention was made with government support under EY030766 awarded by the National Institutes of Health. The government has certain rights in the invention.

DESCRIPTION OF THE TEXT FILE SUBMITTED ELECTRONICALLY

The contents of the text file submitted electronically herewith are incorporated by reference in their entirety. A computer readable format copy of the Sequence Listing: filename: CERA-011_01US_SeqListAmended_ST25.txt, date recorded: Dec. 22, 2020, file size 21.1 kilobytes.

FIELD

The present disclosure relates to anti-ceramide compositions and methods of use thereof for the treatment of diabetic retinopathy.

BACKGROUND

Diabetic retinopathy (DR) affects blood vessels in the light-sensitive tissue called the retina that lines the back of the eye. It is the most common cause of vision loss among people with diabetes and the leading cause of vision impairment and blindness among working-age adults. A consequence of diabetic retinopathy is swelling in an area of the retina called the macula, termed diabetic macular edema (DME).

Existing treatments for DR and DME include anti-VEGF immunotherapy, which has some efficacy in treating both neovascular diabetic retinopathy (DR) and diabetic macular edema (DME). However, several large clinical studies reveal that about 40% of patients do not respond to anti-VEGF therapy. Moreover, anti-VEGF treatment is directed at the very late stage in the disease, when full reversal of retinal damage is difficult.

There remains an unmet need for safe and effective treatments for DR and DME.

BRIEF DESCRIPTION OF DRAWINGS

FIG. 2A shows the change in cytokine expression for TNFα, IL-1β, IL6, ICAM-1, VCAM-1, and MCP1 in the following order: control eyes (white bars), I/R eyes (black bar), and I/R eyes with anti-ceramide scFv administration (gray bars) relative to Cyclophilin A expression. FIG. 2B shows retinal vascular permeability as demonstrated via fluorescence microscopy images and quantitative bar graph analysis in control eyes (left panel, left bar), I/R eyes (middle panel, middle bar) and I/R eyes with anti-ceramide scFv administration (right panel, right bar). The scale bars in the images represent 50 μm.

SUMMARY

Figure 1:
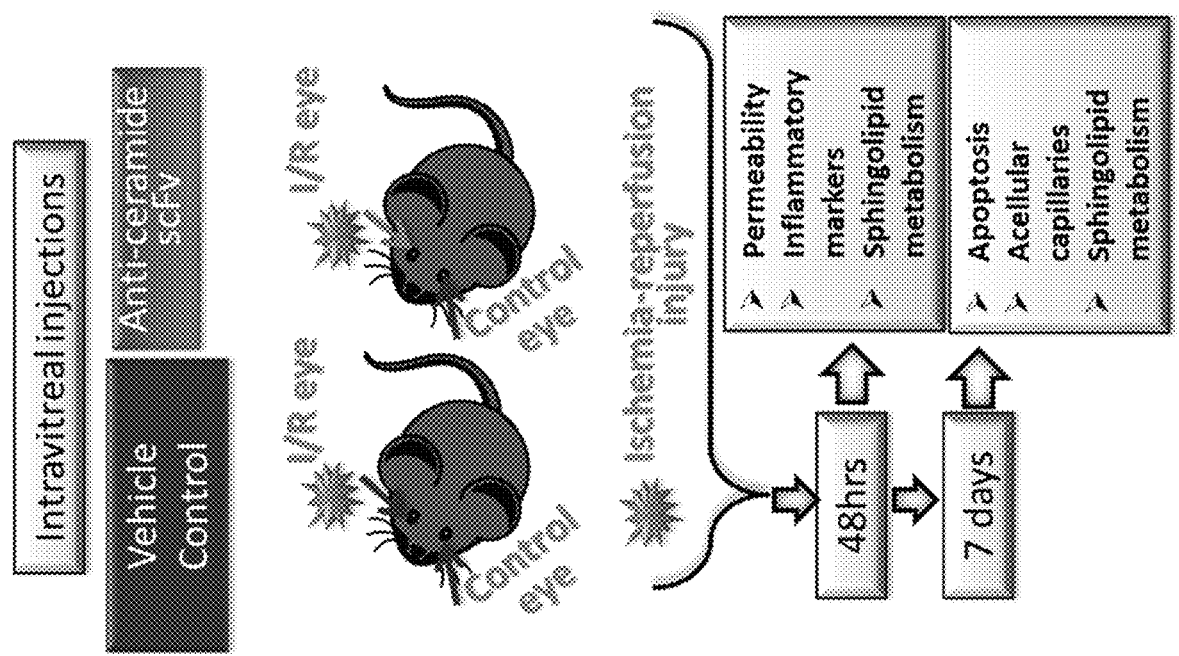
FIG. 1 shows an exemplary experimental design for measuring the effect of intravitreal anti-ceramide scFv administration in a murine model of diabetic retinopathy involving ischemia-reperfusion (I/R) injury.

The present disclosure relates to methods for treating diabetic retinopathy comprising ocularly administering an anti-ceramide antibody or antigen-binding fragment thereof. Also provided are methods for treating subjects who have previously received treatment for diabetic retinopathy. The disclosure further provides methods of treating diabetic retinopathy with a single dose of an anti-ceramide antibody or antigen-binding fragment thereof. Additionally provided is a method of treating diabetic retinopathy with two or more doses of an anti-ceramide antibody or antigen-binding fragment thereof separated by a period of at least two weeks to at least one year. Another aspect of the disclosure relates to a method of treating an ocular inflammatory disease with an anti-ceramide antibody or antigen-binding fragment thereof.

In some embodiments, the present disclosure provides a method of treating or preventing diabetic retinopathy in a subject in need thereof comprising ocularly administering an anti-ceramide antibody or antigen-binding fragment thereof to the subject. In some embodiments, the anti-ceramide antibody or antigen-binding fragment thereof is a single-chain variable fragment (scFv).

In some embodiments, the ocular administration is selected from the group consisting of topical administration, intraocular administration, subconjunctival administration, intracameral administration, injection into the anterior chamber via the temporal limbus, intrastromal administration, intracorneal administration, subretinal administration, aqueous humor injection, subtenon administration, administration to the suprachoroidal space (SCS), administration to the supraciliary space, and intravitreal administration. In some embodiments, the administration is intravitreal administration.

In some embodiments, the subject has received a prior treatment for diabetic retinopathy. In some embodiments, the subject failed to respond to the prior treatment for diabetic retinopathy. In some embodiments, the prior treatment is a therapeutic procedure selected from a vitrectomy and laser surgery, or a therapeutic agent selected from a steroid and an anti-vascular endothelial growth factor (VEGF) therapy. In some embodiments, the anti-VEGF therapy is an anti-VEGF antibody selected from the group consisting of bevacizumab, ranibizumab, and aflibercept.

In some embodiments, the anti-ceramide antibody or antigen-binding fragment thereof is administered as a single dose. In some embodiments, the anti-ceramide antibody or antigen-binding fragment thereof is administered in two or more doses separated by at least two weeks, at least three weeks, or at least four weeks. In some embodiments, the anti-ceramide antibody or antigen-binding fragment thereof is administered in two or more doses separated by about two weeks to about four weeks. In some embodiments, the anti-ceramide antibody or antigen-binding fragment thereof is administered in two or more doses separated by at least one month, at least two months, at least three months, at least four months, at least five months, at least six months, at least seven months, at least eight months, at least nine months, at least ten months, or at least eleven months. In some embodiments, the anti-ceramide antibody or antigen-binding fragment thereof is administered in two or more doses separated by about one month to about six months. In some embodiments, the anti-ceramide antibody or antigen-binding fragment thereof is administered in two or more doses separated by at least one year. In some embodiments, the anti-ceramide antibody or antigen-binding fragment thereof is administered before the onset of one or more symptoms of diabetic retinopathy. In some embodiments, the anti-ceramide antibody or antigen-binding fragment thereof is administered after the onset of one or more symptoms of diabetic retinopathy. In some embodiments, the anti-ceramide antibody or antigen-binding fragment thereof is administered during a non-proliferative stage of diabetic retinopathy. In some embodiments, the anti-ceramide antibody or antigen-binding fragment thereof is administered during a proliferative stage of diabetic retinopathy.

In some embodiments, the present disclosure provides a method of treating or preventing diabetic retinopathy in a subject in need thereof comprising administering an anti-ceramide antibody or antigen-binding fragment thereof to the subject, wherein the subject has received a prior treatment for diabetic retinopathy. In some embodiments, the subject failed to respond to the prior treatment for diabetic retinopathy. In some embodiments, the anti-ceramide antibody or antigen-binding fragment thereof is a single-chain variable fragment (scFv).

In some embodiments, the administration is ocular administration. In some embodiments, the ocular administration is selected from the group consisting of topical administration, intraocular administration, subconjunctival administration, intracameral administration, injection into the anterior chamber via the temporal limbus, intrastromal administration, intracorneal administration, subretinal administration, aqueous humor injection, subtenon administration, administration to the suprachoroidal space (SCS), administration to the supraciliary space, and intravitreal administration. In some embodiments, the ocular administration is intravitreal administration.

In some embodiments, the prior treatment was a vitrectomy, laser surgery, a steroid, and/or an anti-vascular endothelial growth factor (VEGF) therapy. In some embodiments, the anti-VEGF therapy is an anti-VEGF antibody selected from the group consisting of bevacizumab, ranibizumab, and aflibercept.

In some embodiments, the anti-ceramide antibody or antigen-binding fragment thereof is administered as a single dose. In some embodiments, the anti-ceramide antibody or antigen-binding fragment thereof is administered in two or more doses separated by at least two weeks, at least three weeks, or at least four weeks. In some embodiments, the anti-ceramide antibody or antigen-binding fragment thereof is administered in two or more doses separated by about two weeks to about four weeks. In some embodiments, the anti-ceramide antibody or antigen-binding fragment thereof is administered in two or more doses separated by at least one month, at least two months, at least three months, at least four months, at least five months, at least six months, at least seven months, at least eight months, at least nine months, at least ten months, or at least eleven months. In some embodiments, the anti-ceramide antibody or antigen-binding fragment thereof is administered in two or more doses separated by about one month to about six months. In some embodiments, the anti-ceramide antibody or antigen-binding fragment thereof is administered in two or more doses separated by at least one year.

In some embodiments, the anti-ceramide antibody or antigen-binding fragment thereof is administered before the onset of one or more symptoms of diabetic retinopathy. In some embodiments, the anti-ceramide antibody or antigen-binding fragment thereof is administered after the onset of one or more symptoms of diabetic retinopathy. In some embodiments, the anti-ceramide antibody or antigen-binding fragment thereof is administered during a non-proliferative stage of diabetic retinopathy. In some embodiments, the anti-ceramide antibody or antigen-binding fragment thereof is administered during a proliferative stage of diabetic retinopathy.

In some embodiments, the present disclosure provides a method of treating or preventing diabetic retinopathy in a subject comprising administering a single dose of an anti-ceramide antibody or antigen-binding fragment thereof to the subject.

In some embodiments, the present disclosure provides a method of treating or preventing diabetic retinopathy in a subject comprising administering two or more doses of an anti-ceramide antibody or antigen-binding fragment thereof to the subject, wherein the two or more doses are separated by at least two weeks. In some embodiments, the anti-ceramide antibody or antigen-binding fragment thereof is administered in two or more doses separated by at least two weeks, at least three weeks, or at least four weeks. In some embodiments, the anti-ceramide antibody or antigen-binding fragment thereof is administered in two or more doses separated by about two weeks to about four weeks. In some embodiments, the anti-ceramide antibody or antigen-binding fragment thereof is administered in two or more doses separated by at least one month, at least two months, at least three months, at least four months, at least five months, at least six months, at least seven months, at least eight months, at least nine months, at least ten months, or at least eleven months. In some embodiments, the anti-ceramide antibody or antigen-binding fragment thereof is administered in two or more doses separated by about one month to about six months. In some embodiments, the anti-ceramide antibody or antigen-binding fragment thereof is administered in two or more doses separated by at least one year.

In some embodiments, the anti-ceramide antibody or antigen-binding fragment thereof is a single-chain variable fragment (scFv).

In some embodiments, the administration is ocular administration. In some embodiments, the ocular administration is selected from the group consisting of topical administration, intraocular administration, subconjunctival administration, intracameral administration, injection into the anterior chamber via the temporal limbus, intrastromal administration, intracorneal administration, subretinal administration, aqueous humor injection, subtenon administration, administration to the suprachoroidal space (SCS), administration to the supraciliary space, or intravitreal administration. In some embodiments, the ocular administration is intravitreal administration.

In some embodiments, the subject has received a prior treatment for diabetic retinopathy. In some embodiments, the subject failed to respond to the prior treatment for diabetic retinopathy. In some embodiments, the prior treatment was a vitrectomy, laser surgery, a steroid, and/or an anti-vascular endothelial growth factor (VEGF) therapy. In some embodiments, the anti-VEGF therapy is an anti-VEGF antibody selected from the group consisting of bevacizumab, ranibizumab, and aflibercept.

In some embodiments, the anti-ceramide antibody or antigen-binding fragment thereof is administered before the onset of one or more symptoms of diabetic retinopathy. In some embodiments, the anti-ceramide antibody or antigen-binding fragment thereof is administered after the onset of one or more symptoms of diabetic retinopathy. In some embodiments, the anti-ceramide antibody or antigen-binding fragment thereof is administered during a non-proliferative stage of diabetic retinopathy. In some embodiments, the anti-ceramide antibody or antigen-binding fragment thereof is administered during a proliferative stage of diabetic retinopathy.

In some embodiments, the present disclosure provides a method of treating an ocular inflammatory disease comprising ocularly administering an anti-ceramide antibody or antigen-binding fragment thereof. In some embodiments, the anti-ceramide antibody or antigen-binding fragment thereof is a single-chain variable fragment (scFv).

In some embodiments, the ocular administration is selected from the group consisting of topical administration, intraocular administration, subconjunctival administration, intracameral administration, injection into the anterior chamber via the temporal limbus, intrastromal administration, intracorneal administration, subretinal administration, aqueous humor injection, subtenon administration, administration to the suprachoroidal space (SCS), administration to the supraciliary space, or intravitreal administration. In some embodiments, the ocular inflammatory disease is selected from the group consisting of retinal neovascularization, choroidal neovascularization, corneal neovascularization, macular degeneration, age-related macular degeneration, diabetic retinopathy, vitreous hemorrhage, retinal hemorrhage, chorioiditis, neovascular glaucoma, choroid diseases, telangiectasia, retinal artery occlusion, retinal vein occlusion, chorioretinitis, epiretinal membrane, choroid neoplasms, retinopathy of prematurity, cystoid macular edema, papilledema, recurrent ischemia, eye hemorrhage, and proliferative vitreoretinopathy.

In some embodiments, the ocular administration is intravitreal administration.

In some embodiments, the subject has received a prior treatment for diabetic retinopathy. In some embodiments, the subject failed to respond to the prior treatment for diabetic retinopathy. In some embodiments, the prior treatment was therapeutic procedure selected from a vitrectomy and laser surgery, or a therapeutic agent selected from a steroid and an anti-vascular endothelial growth factor (VEGF) therapy. In some embodiments, the anti-VEGF therapy is an anti-VEGF antibody selected from the group consisting of bevacizumab, ranibizumab, and aflibercept.

In some embodiments, the anti-ceramide antibody or antigen-binding fragment thereof is administered as a single dose. In some embodiments, the anti-ceramide antibody or antigen-binding fragment thereof is administered in two or more doses separated by at least two weeks, at least three weeks, or at least four weeks. In some embodiments, the anti-ceramide antibody or antigen-binding fragment thereof is administered in two or more doses separated by about two weeks to about four weeks. In some embodiments, the anti-ceramide antibody or antigen-binding fragment thereof is administered in two or more doses separated by at least one month, at least two months, at least three months, at least four months, at least five months, at least six months, at least seven months, at least eight months, at least nine months, at least ten months, or at least eleven months. In some embodiments, the anti-ceramide antibody or antigen-binding fragment thereof is administered in two or more doses separated by about one month to about six months. In some embodiments, the anti-ceramide antibody or antigen-binding fragment thereof is administered in two or more doses separated by at least one year.

In some embodiments, the anti-ceramide antibody or antigen-binding fragment thereof is administered before the onset of one or more symptoms of the ocular inflammatory disease. In some embodiments, the anti-ceramide antibody or antigen-binding fragment thereof is administered after the onset of one or more symptoms of the ocular inflammatory disease.

In some embodiments, the anti-ceramide antibody or antigen-binding fragment thereof comprises a variable heavy chain ($V_H$) and a variable light chain ($V_L$), wherein the $V_H$ comprises a heavy chain complementarity determining region 1 (HCDR1) comprising the amino acid sequence of GYTFTDHTIH (SEQ ID NO: 1), an HCDR2 comprising the amino acid sequence of YNYPRDGSTKYNEKFKG (SEQ ID NO: 2), and an HCDR3 comprising the amino acid sequence of GFITTVVPSAY (SEQ ID NO: 3), and wherein the $V_L$ comprises a light chain complementarity determining region 1 (LCDR1) comprising the amino acid sequence of RASKSISKYLA (SEQ ID NO: 4), an LCDR2 comprising the amino acid sequence of SGSTLQS (SEQ ID NO: 5), and an LCDR3 comprising the amino acid sequence of QQHNEYPWT (SEQ ID NO: 6). In some embodiments, the $V_H$ comprises the amino acid sequence of SEQ ID NO: 7 and wherein the $V_L$ comprises the amino acid sequence of SEQ ID NO: 8. In some embodiments, the anti-ceramide antibody or antigen-binding fragment thereof is a 6B5 antibody. In some embodiments, the anti-ceramide antibody or antigen-binding fragment thereof is a 6B5 scFv.

In some embodiments, the anti-ceramide antibody or antigen-binding fragment thereof comprises a variable heavy chain ($V_H$) and a variable light chain ($V_L$), wherein the $V_H$ comprises a heavy chain complementarity determining region 1 (HCDR1) comprising the amino acid sequence of NYWMH (SEQ ID NO: 33), an HCDR2 comprising the amino acid sequence of AIYPGDSDTSYNQKFKG (SEQ ID NO: 34), and an HCDR3 comprising the amino acid sequence of LYYGYD (SEQ ID NO: 35), and wherein the $V_L$ comprises a light chain complementarity determining region 1 (LCDR1) comprising the amino acid sequence of KSSQSLIDSDGKTFLN (SEQ ID NO: 36), an LCDR2 comprising the amino acid sequence of LVSKLDS (SEQ ID NO: 37), and an LCDR3 comprising the amino acid sequence of WQGTHFPYT (SEQ ID NO: 38). In some embodiments, the $V_H$ comprises the amino acid sequence of SEQ ID NO: 39 and wherein the $V_L$ comprises the amino acid sequence of SEQ ID NO: 40. In some embodiments, the anti-ceramide antibody or antigen-binding fragment thereof is a 2A2 antibody. In some embodiments, the anti-ceramide antibody or antigen-binding fragment thereof is a 2A2 scFv.

In some embodiments, preventing diabetic retinopathy or the ocular inflammatory disease comprises delaying the onset of diabetic retinopathy or the ocular inflammatory disease. In some embodiments, one or more symptoms of diabetic retinopathy or the ocular inflammatory disease are reduced in the subject compared to a control subject or compared to the subject prior to treatment with the anti-ceramide antibody or antigen-binding fragment thereof. In some embodiments, the one or more symptoms of diabetic retinopathy or the ocular inflammatory disease are selected from retinal inflammation, acellular capillary formation, retinal neovascularization, retinal endothelial cell death, retinal vascular permeability, retinal ischemia-reperfusion injury, retinal leakage area, and occludin disruption. In some embodiments, the one or more symptoms of diabetic retinopathy or the ocular inflammatory disease are reduced by at least 10%, at least 20%, at least 30%, at least 40%, or at least 50% compared to the control subject or compared to the subject prior to treatment with the anti-ceramide antibody or antigen-binding fragment thereof.

In some embodiments, the expression level of one or more inflammatory markers in the eye is reduced compared to the expression level in the eye of a control subject or compared to the expression level in the subject's eye prior to treatment with the anti-ceramide antibody or antigen-binding fragment thereof. In some embodiments, the one or more inflammatory markers is selected from a cytokine, a growth factor, and an adhesion molecule. In some embodiments, the cytokine is selected from TNFα, IL-1β, IL-6, or MCP1. In some embodiments, the growth factor is VEGF. In some embodiments, the adhesion molecule is ICAM-1 or VCAM-1. In some embodiments, the expression level of the one or more inflammatory markers in the subject's eye is decreased by at least 10%, at least 20%, at least 30%, at least 40%, or at least 50% compared to the expression level in the eye of a control subject or compared to the expression level in the subject's eye prior to treatment with the anti-ceramide antibody or antigen-binding fragment thereof.

In some embodiments, one or more vision parameters are increased in the subject compared to the vision parameters a control subject or compared to the vision parameters of the subject prior to treatment with the anti-ceramide antibody or antigen-binding fragment thereof. In some embodiments, the one or more vision parameters are selected from peripheral vision; night vision; color vision; distance vision; close-range vision; and vision clarity.

DETAILED DESCRIPTION

Overview

The present disclosure relates to compositions and methods for treating diabetic retinopathy. In some embodiments, provided are compositions of anti-ceramide antibodies and antigen-binding fragments thereof (e.g., scFvs) and methods of use in the treatment or prevention of diabetic retinopathy. Such compositions and methods may be used in the treatment of diabetic retinopathy in patients who have previously failed another treatment for diabetic retinopathy, e.g. anti-VEGF antibody therapy. Further provided is a method for administering anti-ceramide scFv intravitreally.

Definitions

As used in this specification and the appended claims, the singular forms "a," "an," and "the" include plural references unless the content clearly dictates otherwise.

As used in this specification, the term "and/or" is used in this disclosure to mean either "and" or "or" unless indicated otherwise.

Throughout this specification, unless the context requires otherwise, the words "comprise", or variations such as "comprises" or "comprising", will be understood to imply the inclusion of a stated element or integer or group of elements or integers but not the exclusion of any other element or integer or group of elements or integers.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 10% or less in either direction (greater than or less than) of the stated reference value unless otherwise stated or otherwise evident from the context (except where such number would exceed 100% of a possible value or fall below 0% of a possible value).

The term "sample" refers to a biological composition (e.g., a cell or a portion of a tissue) that is subjected to analysis and/or modification. In some embodiments, a sample is a "primary sample" in that it is obtained directly from a subject; in some embodiments, a "sample" is the result of processing of a primary sample, for example to remove certain components and/or to isolate or purify certain components of interest.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein. In some embodiments, the subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g. mice, rats, guinea pigs, hamsters, rabbits, etc.) may be used for experimental investigations.

As used herein, the terms "treatment," "treating," or "ameliorating" refers to either a therapeutic treatment or prophylactic/preventative treatment. A treatment is therapeutic if at least one symptom of disease in an individual receiving treatment improves or a treatment can delay worsening of a progressive disease in an individual, or prevent onset of additional associated diseases.

As used herein, the term "effective amount" refers to the minimum amount of an agent or composition required to result in a particular physiological effect. The effective amount of a particular agent may be represented in a variety of ways based on the nature of the agent, such as mass/volume, # of cells/volume, particles/volume, (mass of the agent)/(mass of the subject), # of cells/(mass of subject), or particles/(mass of subject). The effective amount of a particular agent may also be expressed as the half-maximal effective concentration ($EC_{50}$), which refers to the concentration of an agent that results in a magnitude of a particular physiological response that is half-way between a reference level and a maximum response level.

The term "antibody" refers to an immunoglobulin (Ig) molecule capable of binding to a specific target, such as a carbohydrate, polynucleotide, lipid, or polypeptide, through at least one epitope recognition site located in the variable region of the Ig molecule. As used herein, the term encompasses intact polyclonal or monoclonal antibodies and antigen-binding fragments thereof. For example, a native immunoglobulin molecule is comprised of two heavy chain polypeptides and two light chain polypeptides. Each of the heavy chain polypeptides associate with a light chain polypeptide by virtue of interchain disulfide bonds between the heavy and light chain polypeptides to form two heterodimeric proteins or polypeptides (i.e., a protein comprised of two heterologous polypeptide chains). The two heterodimeric proteins then associate by virtue of additional interchain disulfide bonds between the heavy chain polypeptides to form an immunoglobulin protein or polypeptide.

The term "antigen-binding fragment" as used herein refers to a polypeptide fragment that contains at least one Complementarity-determining region (CDR) of an immunoglobulin heavy and/or light chain that binds to at least one epitope of the antigen of interest. In this regard, an antigen-binding fragment of the herein described antibodies may comprise 1, 2, 3, 4, 5, or all 6 CDRs of a variable heavy chain (VH) and variable light chain (VL) sequence from antibodies that specifically bind ceramide. Antigen-binding fragments include proteins that comprise a portion of a full length antibody, generally the antigen binding or variable region thereof, such as Fab, F(ab')2, Fab', Fv fragments, minibodies, diabodies, single domain antibody (dAb), single-chain variable fragments (scFv), multispecific antibodies formed from antibody fragments, and any other modified configuration of the immunoglobulin molecule that comprises an antigen-binding site or fragment of the required specificity. In certain embodiments of the disclosure, an antigen-binding fragment, rather than an intact antibody, is used to increase tissue penetration or tumor penetration. In other embodiments, antigen-binding fragments are further modified to increase serum half-life.

"Fc region" or "Fc domain" refers to a polypeptide sequence corresponding to or derived from the portion of an antibody that is capable of binding to Fc receptors on cells and/or the C1q component of complement, thereby mediating the effector function of an antibody. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc region is a homodimeric protein comprising two polypeptides that are associated by disulfide bonds, and each comprising a hinge region, a CH2 domain, and a CH3 domain. However, more recently the term has been applied to the single chain monomer component consisting of CH3, CH2, and at least a portion of the hinge sufficient to form a disulfide-linked dimer with a second such chain. As such, and depending on the context, use of the terms "Fc region" or "Fc domain" will refer herein to either the dimeric form or the individual monomers that associate to form the dimeric protein. For a review of immunoglobulin structure and function, see Putnam, The Plasma Proteins, Vol. V (Academic Press, Inc., 1987), pp. 49-140; and Padlan, Mol. Immunol. 31:169-217, 1994. As used herein, the term Fc domain includes variants of naturally occurring sequences.

The term "immunoglobulin constant region" or "constant region" refers to a peptide or polypeptide sequence that corresponds to or is derived from part or all of one or more constant domains of an immunoglobulin (e.g., CH1, CH2, CH3). In certain embodiments, the constant region does not comprise a CH1 domain. In certain embodiments, the constant domains making up the constant region are human The terms "light chain variable region" (also referred to as "light chain variable domain" or "VL") and "heavy chain variable region" (also referred to as "heavy chain variable domain" or "VH") refer to the variable binding region from an antibody light and heavy chain, respectively. The variable binding regions are made up of discrete, well-defined subregions known as "complementarity determining regions" (CDRs) and "framework regions" (FRs).

The term "immunoglobulin light chain constant region" (also referred to as "light chain constant region" or "CL") is a constant region from an antibody light chain.

The term "immunoglobulin heavy chain constant region" (also referred to as "heavy chain constant region" or "CH") refers to the constant region from the antibody heavy chain. The CH is further divisible, depending on the antibody isotype into CH1, CH2, and CH3 (IgA, IgD, IgG), or CH1, CH2, CH3, and CH4 domains (IgE, IgM).

The term "F(ab)" refers to two of the protein fragments resulting from proteolytic cleavage of IgG molecules by the enzyme papain. Each F(ab) comprises a covalent heterodimer of the VH chain and VL chain and includes an intact antigen-binding site. Each F(ab) is a monovalent antigen-binding fragment. The term "Fab'" refers to a fragment derived from F(ab')2 and may contain a small portion of Fc. Each Fab' fragment is a monovalent antigen-binding fragment.

The term "F(ab')2" refers to a protein fragment of IgG generated by proteolytic cleavage by the enzyme pepsin. Each F(ab')2 fragment comprises two F(ab') fragments and is therefore a bivalent antigen-binding fragment.

An "Fd fragment" comprises the VH and CH1 domains.

An "Fv fragment" refers to a non-covalent VH::VL heterodimer which includes an antigen-binding site that retains much of the antigen recognition and binding capabilities of the native antibody molecule, but lacks the CH1 and CL domains contained within a Fab. Inbar et al. (1972) Proc. Nat. Acad. Sci. USA 69:2659-2662; Hochman et al. (1976) Biochem 15:2706-2710; and Ehrlich et al. (1980) Biochem 19:4091-4096. In some embodiments, the Fv fragment can be produced by preferential proteolytic cleavage of an IgM, and on rare occasions of an IgG or IgA immunoglobulin molecule. Fv fragments are, however, more commonly derived using recombinant techniques known in the art.

A "dAb fragment" (Ward et al., Nature 341:544 546, 1989) comprises a VH domain.

A "single-chain antibody" or an "scFv" is a fusion protein of the variable regions of the heavy (VH) and light chains (VL) of immunoglobulins, connected with a short linker peptide of ten to about 25 amino acids. The linker may be rich in glycine for flexibility, as well as serine or threonine for solubility, and can either connect the N-terminus of the VH with the C-terminus of the VL, or vice versa. The scFv retains the specificity of the original immunoglobulin, despite removal of the constant regions and the introduction of the linker. In the present disclosure, any mention of antibodies or antibody fragments or the use thereof is intended to comprise scFv molecules and the use thereof.

"Minibodies" refer to a fusion protein comprising an scFv joined to a CH3 domain and are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "diabody" refers to a bispecific antibody in which VH and VL domains are expressed in a single polypeptide chain using a linker that is too short to allow for pairing between the two domains on the same chain, thereby forcing the domains to pair with complementary domains of another chain and creating two antigen-binding sites (see, e.g., Holliger et al., Proc. Natl. Acad. Sci. USA 90:6444-48 (1993) and Poljak et al., Structure 2:1121-23 (1994)).

The term "nanobody" or a "single domain antibody" refers to an antigen-binding fragment consisting of a single monomeric variable antibody domain. The Nanoclone method is a method for generating Nanobodies against a desired target based on automated high-throughput selection of B-cells. (See, WO 2006/079372)

The term "monoclonal antibody" as used herein refers to an antibody obtained from a population of substantially homogeneous antibodies, i.e., the individual antibodies comprising the population are identical except for possible naturally occurring mutations that may be present in minor amounts.

The term "chimeric antibody" as used herein refers to a monoclonal antibody in which a portion of the heavy and/or light chain is identical or homologous to corresponding sequences in antibodies derived from a particular species or belonging to a particular antibody class or subclass, while the remainder of the chain(s) is identical or homologous to corresponding sequences in antibodies derived from another species or belonging to another antibody class or subclass, as well as fragments of such antibodies, so long as they exhibit the desired biological activity.

The term "single chain variable fragment" or "scFv" refers to a fusion protein of the variable regions of the heavy (VH) and light chains (VL) of immunoglobulins, connected with a short linker peptide of ten to about 25 amino acids. Huston et al. (1988) *Proc. Nat. Acad. Sci. USA* 85(16):5879-5883. The linker can connect the N-terminus of the VH with the C-terminus of the VL, or vice versa. A number of methods have been described to discern chemical structures for converting the naturally aggregated—but chemically separated—light and heavy polypeptide chains from an antibody V region into an scFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

As used herein, the term "CDR" refers to the "complementarity determining region" of an immunoglobulin (antibody) molecule. CDRs are part of the variable domain in an antibody where the antibody binds to its specific antigen. There are three CDR per variable domain (i.e., CDR1, CDR2 and CDR3 in the variable domain of the light chain and CDR1, CDR2 and CDR3 in the variable domain of the heavy chain). Within the variable domain, CDR1 and CDR2 are found in the variable (V) region of a polypeptide chain, CDR3 shows the greatest variability as it is encoded by a recombination of the VJ in the case of a light chain region and VDJ in the case of heavy chain regions.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

As used herein, the term "humanized" refers to an antibody or antigen-binding fragment thereof derived from a non-human species that retains the antigen-binding properties of the original non-human antibody. In some embodiments, the binding fragments of an antibody (e.g., light and heavy chain variable regions, Fab, scFv) are humanized. Non-human antigen-binding fragments can be humanized using techniques known as CDR grafting (Jones et al., Nature 321:522 (1986)) and variants thereof, including "reshaping" (Verhoeyen, et al., 1988 Science 239:1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312). If derived from a non-human source, other regions of the antibody, such as the hinge region and constant region domains, can also be humanized.

As used herein, the term "pharmaceutically acceptable" refers to molecular entities and compositions that do not generally produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

The terms "prevent," "prophylaxis," and "prophylactically" refer to the administration of a compound, e.g. an anti-ceramide antibody or antigen-binding fragment thereof prior to the onset of disease (e.g., prior to the onset of certain symptoms of a disease). Preventing disease may include reducing the likelihood that the disease will occur, delaying onset of the disease, ameliorating long term symptoms, or delaying eventual progression of the disease.

Herein, the term "specifically binds" refers to the ability of an antibody or antigen-binding fragment thereof to bind a target antigen with a binding affinity (Ka) of at least $10^5$ $M^{-1}$ while not significantly binding other components or antigens present in a mixture. Reference to an anti-ceramide antibody herein refers to an antibody or antigen-binding fragment thereof that specifically binds to ceramide.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage sequence identity is calculated by determining the number of positions at which the identical nucleic acid base or amino acid residue occurs in both sequences to yield the number of identical positions. The number of identical positions is then divided by the total number of positions in the comparison window and multiplied by 100 to yield the percentage of sequence identity. Percentage of sequence identity is determined by comparing two optimally aligned sequences over a comparison window. The comparison window for polynucleotide sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

"Angiogenesis" refers to the formation of new blood vessels.

As used herein, the term "ocular" or "ocularly" refers to administration of a medicament to the eye and surrounding tissue. For example, in some embodiments ocular administration comprises: topical administration (such as administration to the surface of the eye e.g., sclera), intraocular administration, subconjunctival (such as under the eyeball conjunctiva or underneath the conjunctiva lining of the eyelid administration), intracameral administration, injection into the anterior chamber via the temporal limbus, intrastromal administration, intracorneal administration, subretinal administration, aqueous humor injection, sub-tenon administration, administration to the suprachoroidal space (SCS), administration to the supraciliary space, or intravitreal administration.

Anti-Ceramide Antibodies, Antibody Fragments, and Derivatives

The present disclosure relates to anti-ceramide antibodies and antigen-binding fragments thereof for the treatment of diabetic retinopathy. Ceramides are a family of waxy lipid molecules. A ceramide is composed of sphingosine and a fatty acid. Ceramides are found in high concentrations within the cell membrane of eukaryotic cells, since they are component lipids that make up sphingomyelin, one of the major lipids in the lipid bilayer. Ceramide participates in a variety of cellular signaling, including regulating differentiation, proliferation, and programmed cell death (PCD) of cells. As a bioactive lipid, ceramide has been implicated in a variety of physiological functions including apoptosis, cell growth arrest, differentiation, cell senescence, cell migration and adhesion. Roles for ceramide and its downstream metabolites have also been suggested in a number of pathological states including cancer, neurodegeneration, diabetes, microbial pathogenesis, obesity, and inflammation.

Sequences and properties of exemplary anti-ceramide antibodies are also disclosed in U.S. Pat. Pub. No. 2010/0239572 and 2017/0335014, each of which are hereby incorporated by reference. Sequences of illustrative anti-ceramide antibodies are provided in Table 1. However, any anti-ceramide antibody or antigen-binding fragment thereof may be employed according to the disclosed methods and uses.

TABLE 1

Illustrative Anti-Ceramide Antibody Sequences

| Antibody | Component | Sequence | SEQ ID |
|---|---|---|---|
| 6B5 | HCDR1 | GYTFTDHTIH | 1 |
| 6B5 | HCDR2 | YNYPRDGSTKYNEKFKG | 2 |
| 6B5 | HCDR3 | GFITTVVPSAY | 3 |
| 6B5 | LCDR1 | RASKSISKYLA | 4 |
| 6B5 | LCDR2 | SGSTLQS | 5 |
| 6B5 | LCDR3 | QQHNEYPWT | 6 |
| 6B5 | VH | QVQLQQSDAELVKPGASVKISCKVSGYTFTDHTIHWMKQRPEQGLEWIGYNPRDGSTKYNEKFGKATLTDADKSSSTAYMQLNSLTSEDSAVYFCAKGFITTVVPSAYWGQGTLVTVSA | 7 |
| 6B5 | VL | DVQITQSPSYLAASPGETITINCRASKSISKYLAWYQEKPGKTNKLLIYSGSTLQSGIPSRFSGSGSGTDFTLTISSLEPEDFAMYYCQQHNEYPWTFGGGTKLEIK | 8 |
| 6C8 | HCDR1 | GYAFSSYWMN | 9 |
| 6C8 | HCDR2 | QIYPGDGDTNYNGKFKG | 10 |
| 6C8 | HCDR3 | RCYYGLYFDV | 11 |
| 6C8 | LCDR1 | KASQDINRYLS | 12 |
| 6C8 | LCDR2 | RLVD | 13 |

TABLE 1-continued

Illustrative Anti-Ceramide Antibody Sequences

| Antibody | Component | Sequence | SEQ ID |
|---|---|---|---|
| 6C8 | LCDR3 | LQYDEFPYT | 14 |
| 6C8 | VH | QVQLQQSGAELVKPGASVKISCKASGYAFSSYWMNWVKQRP GKGLEWIGQIYPGDGDTNYNGKFKGKATLTADKSSSTAYMQ LSSLTSEDSAVYFCTRRCYYGLYFDVWGTGTTVTVSS | 15 |
| 6C8 | VL | DIKMTQSPSSRYASLGERVTITCKASQDINRYLSWFQQKPG KSPKTLIYRANRLVDGVPSSRFSGSGSGQDYSLTISSLEYE DMGIYYCLQYDEFPYTFGGGTKLEIK | 16 |
| 7B10 | HCDR1 | GYTFTSYWMH | 17 |
| 7B10 | HCDR2 | YINPSSGYTKYNQFKD | 18 |
| 7B10 | HCDR3 | GGYYGFAY | 19 |
| 7B10 | LCDR1 | SASSSVSYMY | 20 |
| 7B10 | LCDR2 | LTSNLAS | 21 |
| 7B10 | LCDR3 | QQWSSNPLT | 22 |
| 7B10 | VH | QVQLQQSGAELAKPGASVKLSCKASGYTFTSYWMHWVKQRP GQGLEWIGYINPSSGYTKYNQFKDKATLTADKSSSTAYMQ LSSLTYEDSAVYYCARGGYYGFAYWGQGTLVTVSA | 23 |
| 7B10 | VL | QIVLTQSPALMSASPGEKVTMTCSASSSVSYMYWYQQKPRS SPKPWIYLTSNLASGVPARFSGSGSGTSYSLTISSMEAEDA ATYYCQQWSSNPLTFGAGTKLELK | 24 |
| 9H10 | HCDR1 | GFSLTGYGVH | 25 |
| 9H10 | HCDR2 | VIWSGGSTDYNAAFIS | 26 |
| 9H10 | HCDR3 | NYGYDYAMDY | 27 |
| 9H10 | LCDR1 | RASQSIGTSIH | 28 |
| 9H10 | LCDR2 | YASESIS | 29 |
| 9H10 | LCDR3 | QQSNSWPFT | 30 |
| 9H10 | VH | QVQLKQSGPGVQPSSLSITCTVSGFSLTSYGVHWVRQSPGK GLEWLGVIWSGGSTDYNAAFISRLSISKDNSKSQVFFKMNS LQADDTAIYYCARNYGYDYAMDYWGQGTSVTVSS | 31 |
| 9H10 | VL | DILLTQSPAILSVSPGERVSFSCRASQSIGTSIHWYQQRTN GSPRLLIKYASESISGIPSRFSGSGSGTDFTLSINSVESED IADYYCQQSNSWPFTFGSGTKLEIK | 32 |
| 2A2 | HCDR1 | NYWMH | 33 |
| 2A2 | HCDR2 | AIYPGDSDTSYNQKFKG | 34 |
| 2A2 | HCDR3 | LYYGYD | 35 |
| 2A2 | LCDR1 | KSSQSLIDSDGKTFLN | 36 |
| 2A2 | LCDR2 | LVSKLDS | 37 |
| 2A2 | LCDR3 | WQGTHFPYT | 38 |
| murine 2A2 | VH | EVQLQQSGTVLARPGASVKMSCKASGYTFTNYWMHWVKQRP VQGLEWIGAIYPGDSDTSYNQKFKGKAKLTAVTSTSTAFME LSSLTNEDSAVYYCTGLYYGYDWGQGTTLTVSS | 39 |
| murine 2A2 | VL | DVLMTQTPLTLSVTIGQPASISCKSSQSLIDSDGKTFLNWL LQRPGQSPKRLIYLVSKLDSGVPDRFTGSGSGTDFTLKISR VEAEDLGLYYCWQGTHFPYTFGGGTKLEIK | 40 |
| humanized 2A2 | Heavy chain | MDWTWRVFCLLAVAPGAHSQVQLVQSGAEVKKPGASVKVSC KASGYTFTNYWMHWVRQAPGQGLEWMGAIYPGDSDTSYNQK FKGRVTMTRDTSTSTVYMELSSLRSEDTAVYYCARLYYGYD WGQGTTVTVSSASTKGPSVFPLAPSSKSTSGGTAALGCLVK DYFPEPVTVSWNSGALTSGVHTFPAVLQSSGLYSLSSVVTV | 41 |

TABLE 1-continued

Illustrative Anti-Ceramide Antibody Sequences

| Antibody | Component | Sequence | SEQ ID |
|---|---|---|---|
| | | PSSSLGTQTYICNVNHKPSNTKVDKKVEPKSCDKTHTCPPC<br>PAPELLGGPSVFLFPPKPKDTLMISRTPEVTCVVVDVSHED<br>PEVKFNWYVDGVEVHNAKTKPREEQYNSTYRVVSVLTVLHQ<br>DWLNGKEYKCKVSNKALPAPIEKTISKAKGQPREPQVYTLP<br>PSRDELTKNQVSLTCLVKGFYPSDIAVEWESNGQPENNYKT<br>TPPVLDSDGSFFLYSKLTVDKSRWQQGNVFSCSVMHEALHN<br>HYTQKSLSLSPG | |
| h2A2 | Light chain | MRLPAQLLGLLMLWVPGSSGDVVMTQSPLSLPVTLGQPASI<br>SCKSSQSLIDSDGKTFLNWFQQRPGQSPRRLIYLVSKLDSG<br>VPDRFSGSGSGTDFTLKISRVEAEDVGVYYCWQGTHFPYTF<br>GQGTKLEIKRTVAAPSVFIFPPSDEQLKSGTASVVCLLNNF<br>YPREAKVQWKVDNALQSGNSQESVTEQDSKDSTYSLSSTLT<br>LSKADYEKHKVYACEVTHQGLSSPVTKSFNRGEC | 42 |

In some embodiments, the anti-ceramide antibody is selected from the group consisting of a monoclonal antibody, a chimeric antibody, a humanized antibody, a human antibody, a recombinant antibody, or a synthetic antibody. In some embodiments, the anti-ceramide antigen-binding antibody fragment is an antigen-binding fragment of any one of the foregoing. In some embodiments, the anti-ceramide antigen-binding antibody fragment is an Fab fragment, an Fab' fragment, an F(ab')2 fragment, an Fv fragment, an Fd fragment, a dAb fragment, a diabody, an scFv or the like. In some embodiments, the anti-ceramide antibodies and antigen-binding fragments thereof are produced using recombinant DNA technologies. Procedures for the expression and purification of recombinant proteins are well established in the art.

In some embodiments, the anti-ceramide antibody or antigen-binding fragment thereof is a single-chain variable fragment (scFv). In some embodiments, the scFv comprises the CDR sequences and/or the variable chain sequences of the 2A2, 6C8, 7B10, 9H10, or 6B5 antibodies.

In some embodiments, the anti-ceramide antibody or antigen-binding fragment thereof is the 2A2 antibody or an antigen-binding fragment thereof, as described in U.S. Pat. Pub. No. 2010/0239572. In some embodiments, the anti-ceramide antibody or antigen-binding fragment thereof is the 6B5 antibody or an antigen-binding fragment thereof, as described in U.S. Pat. Pub. No. 2017/0335014. In some embodiments, the anti-ceramide antibody or antigen-binding fragment thereof is an scFv. In some embodiments, the scFV comprises the CDR sequences of any of the antibodies disclosed in Table 1. In some embodiments, the scFv comprises the CDR sequences of h2A2. In some embodiments, the scFv comprises the CDR sequences of 6B5. In some embodiments, the scFv comprises the variable heavy and light chain sequences of h2A2. In some embodiments, the scFv comprises the variable heavy and light chain sequences of 6B5.

In some embodiments, an anti-ceramide antibody or antigen-binding fragment thereof has any immunoglobulin isotype. An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In some embodiments, anti-ceramide antibodies or antigen-binding fragments thereof comprise one or more modifications in the Fc region. Certain modifications can provide desired effector functions or serum half-life. In some embodiments, with the appropriate Fc regions, a naked antibody bound on the cell surface can induce cytotoxicity, e.g., via antibody-dependent cellular cytotoxicity (ADCC) or by recruiting complement in complement dependent cytotoxicity (CDC), or by recruiting nonspecific cytotoxic cells that express one or more effector ligands that recognize bound antibody on a target cell and subsequently cause phagocytosis of the target cell in antibody dependent cell-mediated phagocytosis (ADCP), or some other mechanism. Where it is desirable to eliminate or reduce effector function, so as to minimize side effects or therapeutic complications, certain other Fc regions may be used. The Fc region of antibodies can be modified to increase the binding affinity for FcRn and thus increase serum half-life. Alternatively, the Fc region can be conjugated to PEG or albumin to increase the serum half-life, or some other conjugation that results in a desired effect.

In some embodiments, the anti-ceramide antibody or antigen-binding fragment thereof comprises a detectable label or tag. Exemplary detectable labels include fluorescent tags, affinity tags, radioisotopes, luminescent markers, particulate labels, chromophores, phosphorescent markers, and enzyme labels. Exemplary fluorescent labels include GFP, RFP, and YFP. Exemplary enzyme labels include horseradish peroxidase and alkaline phosphatase. Exemplary peptide tags include His-tag, MBP, and streptavidin.

The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, or by ELISA or Western blot.

Diabetic Retinopathy

In some embodiments, the present disclosure provides methods and compositions for treating diabetic retinopathy. Diabetic retinopathy refers to a medical condition in which damage occurs to the retina due to diabetes mellitus. Chronically high blood sugar from diabetes is associated with damage to the tiny blood vessels in the retina, leading to diabetic retinopathy. Diabetic retinopathy can cause blood vessels in the retina to leak fluid or hemorrhage, distorting vision. In its most advanced stage, new abnormal blood vessels proliferate on the surface of the retina, which can lead to scarring and cell loss in the retina.

In some embodiments, the disclosed methods and compositions may be used to treat different stages of diabetic retinopathy. Diabetic retinopathy may progress through a non-proliferative stage, also referred to as early stage, and a proliferative stage, also referred to as late stage.

In some embodiments, the present disclosure provides methods and compositions that may be used to treat diabetic retinopathy during the non-proliferative stage. Non-proliferative diabetic retinopathy (NPDR) may be mild, moderate, or severe. Mild NPDR is characterized by microaneurysms in the retina's blood vessels. These microaneurysms may leak fluid into the retina. As the disease progresses to the moderate NPDR stage, retinal blood vessels can become distorted and lose their ability to transport blood, resulting in characteristic changes to the appearance of the retina and may contribute to diabetic macular edema. At the severe NPDR stage, many more blood vessels are blocked, depriving blood supply to areas of the retina. These areas then secrete pro-angiogenic growth factors. Angiogenic molecules in the eye include VEGF, FGF, PGF, TGF-alpha, TGF-beta, IGF, PDGF, MMPs, HGF/SF, TNF-alpha, CTGF, IL-1, IL-8, MCP-1, leptin, integrins, and angiogenin. In some embodiments, the present methods are characterized by preventing or decreasing one or more markers of diabetic retinopathy. In some embodiments, the present methods may prevent, reduce, inhibit, or lower the level of retinal microaneurysms, retinal fluid leakage, diabetic macular edema, and/or retinal pro-angiogenic growth factors. In some embodiments, one or more of VEGF, FGF, PGF, TGF-alpha, TGF-beta, IGF, PDGF, MMPs, HGF/SF, TNF-alpha, CTGF, IL-1, IL-8, MCP-1, integrins, and angiogenin are decreased by the present methods.

In some embodiments, the present disclosure provides methods and compositions that may be used to treat diabetic retinopathy during the proliferative stage. Proliferative diabetic retinopathy (PDR) is the advanced stage of disease. At this stage, pro-angiogenic growth factors secreted by the retina trigger the proliferation of new blood vessels, which grow along the inside surface of the retina and into the vitreous gel. The new blood vessels are fragile and more likely to leak and bleed. Accompanying scar tissue can contract and cause retinal detachment (i.e., the pulling away of the retina from underlying tissue) which can lead to permanent vision loss. In some embodiments, the present methods may prevent, reduce, inhibit, or lower the level of retinal neovascularization, retinal hemorrhage, retinal scarring, retinal detachment, and vision loss.

In some embodiments, the present disclosure provides methods and compositions that may be used to prevent diabetic retinopathy by administration to a diabetic subject before the onset of diabetic retinopathy, e.g., before the onset of one or more symptoms thereof. Among the most consistent risk factors, duration of diabetes is a strong predictor for development and progression of the retinopathy. Among patients with younger-onset diabetes, the prevalence is estimated at approximately 8% at 3 years, 25% at 5 years, 60% at 10 years, and 80% at 15 years. In some embodiments, the disclosed methods and compositions may be used to delay the onset of diabetic retinopathy, e.g., to more than 3 years, more than 5 years, more than 10 years, or more than 15 years after development of diabetes.

In some embodiments, the disclosed methods and compositions may be used to prevent diabetic retinopathy in a subject at risk for developing diabetic retinopathy, e.g., a subject having one or more risk factors associated with development of diabetic retinopathy. Hyperglycemia, hypertension, hyperlipidemia, and renal disease are considerable risk factors. Male sex, higher severity of diabetes (indicated by use of insulin and oral diabetes treatments versus pills alone or use of pills alone versus no treatment), higher average systolic blood pressure, and higher hemoglobin A1c are additional factors to be considered.

Symptoms and Detection

In some embodiments, the present methods may affect one or more symptoms and/or detectable markers of diabetic retinopathy. The early, non-proliferative stages of diabetic retinopathy usually have no symptoms. In some embodiments, the present methods and compositions are for use in a diabetic subject before the onset of symptoms of diabetic retinopathy. The disease often progresses unnoticed until it affects vision. Bleeding from retinal blood vessels during the early stages of disease can cause the appearance of "floating" spots, which may clear on their own. Without prompt treatment, bleeding often recurs, increasing the risk of permanent vision loss. If diabetic macular edema occurs, it can cause blurred vision. In some embodiments, the present compositions and methods may reduce the incidence, severity, or level of floating spots, retinal bleeding, vision loss, and/or blurred vision. In some embodiments, one or more parameters of vision may be improved by the present methods, including, but not limited to, overall vision, peripheral vision, night vision, color vision, distance vision, close-range vision, and vision clarity.

Diabetic retinopathy and diabetic macular edema may be detected during a comprehensive eye exam that includes visual acuity testing (eye chart tests to measure a subjects ability to see at various distances); tonometry (measurements of pressure inside the eye); pupil dilation; and optical coherence tomography (OCT). During such exam, a physician may check for one or more of the following: changes to retinal blood vessels, including new vessel formation, swelling, and bleeding; leaking retinal blood vessels or warning signs of leaky blood vessels, such as fatty deposits, weakened vessel walls, and bulging vessel walls; swelling of the macula; changes in the lens, including changes in curvature or cataract formation; and damage to nerve tissue.

In some embodiments, the present compositions and methods may be used to treat a subject with any one or more of these symptoms of diabetic retinopathy. In some embodiments, the present compositions and methods may prevent, treat, or improve any one or more of these symptoms. If diabetic macular edema or severe diabetic retinopathy is suspected, a fluorescein angiogram may be used to look for damaged or leaky blood vessels. In this test, a fluorescent dye is injected into the bloodstream, often into an arm vein. Pictures of the retinal blood vessels are taken as the dye reaches the eye. In some embodiments, the present compositions and methods may be used to prevent or lessen the incidence, prevalence, or severity of damaged and/or leaky blood vessels in the eye.

Existing treatments for diabetic retinopathy include anti-VEGF therapy, steroids, laser surgery, and vitrectomy.

Anti-VEGF Injection Therapy. Anti-VEGF drugs are injected into the vitreous gel to block the actions of the pro-angiogenic growth factor VEGF. Blocking VEGF can reverse abnormal blood vessel growth and decrease fluid in the retina. Available anti-VEGF drugs include Avastin® (bevacizumab), Lucentis® (ranibizumab), and Eylea® (aflibercept). Lucentis® (ranibizumab) and Eylea® (aflibercept) are approved by the U.S. Food and Drug Administration (FDA) for treating diabetic macular edema. Avastin® (bevacizumab) was approved by the FDA to treat cancer, but is commonly used to treat eye conditions, including diabetic macular edema. Most people require monthly anti-VEGF injections for the first six months of treatment. Thereafter, injections are needed less often: typically three to four during the second six months of treatment, about four during the second year of treatment, two in the third year, one in the fourth year, and none in the fifth year. Recent studies have shown that anti-VEGF treatment may be effective for treating diabetic macular edema and for slowing progression of diabetic retinopathy, including PDR, so that anti-VEGF is increasingly used as a first-line treatment for PDR. However, several large clinical studies reveal that about 40% of patients do not respond to anti-VEGF therapy. Moreover, anti-VEGF treatment is directed at the very late stage in the disease, when full reversal of retinal damage is difficult.

Laser surgery. In focal/grid macular laser surgery, a few to hundreds of small laser burns are made to leaking blood vessels in areas of edema near the center of the macula. Laser burns for diabetic macular edema slow the leakage of fluid, reducing swelling in the retina. The procedure is usually completed in one session, but some patients may need more than one treatment. Focal/grid laser treatment can be used in combination with anti-VEGF therapy. For example, focal/grid laser treatment is sometimes applied before anti-VEGF injections, sometimes on the same day or a few days after an anti-VEGF injection, and sometimes only when diabetic macular edema fails to improve adequately after six months of anti-VEGF therapy.

PDR may also be treated with scatter laser surgery, sometimes called panretinal laser surgery or panretinal photocoagulation. Treatment involves making 1,000 to 2,000 tiny laser burns in areas of the retina away from the macula. These laser burns are intended to cause abnormal blood vessels to shrink. Although treatment can be completed in one session, two or more sessions are sometimes required. While it can preserve central vision, scatter laser surgery may cause some loss of side (peripheral), color, and night vision. Scatter laser surgery works best before new, fragile blood vessels have started to bleed.

Corticosteroids. Corticosteroids, may be used alone or in combination with other drugs or laser surgery to treat diabetic macular edema. Corticosteroids may be injected or implanted into the eye. The Ozurdex® (dexamethasone) implant is for short-term use, while the Iluvien® (fluocinolone acetonide) implant is longer lasting. Both are biodegradable and release a sustained dose of corticosteroids to suppress diabetic macular edema.

Vitrectomy. A vitrectomy is the surgical removal of the vitreous gel in the center of the eye. The procedure is used to treat severe bleeding into the vitreous, and is performed under local or general anesthesia. A clear salt solution is gently pumped into the eye through one or more ports to maintain eye pressure during surgery and to replace the removed vitreous. The same instruments used during vitrectomy also may be used to remove scar tissue or to repair a detached retina.

Role of Ceramide and ASM in Diabetic Retinopathy

Without wishing to be bound by any one theory, it is believed that the present treatments are able to downregulate retinal inflammatory signaling by selectively inhibiting ceramide in the retina via ocular treatments of anti-ceramide antibodies or antigen binding fragments thereof.

Sphingolipids represent a major component of membrane microdomains, and ceramide-enriched microdomains appear to be a prerequisite for inflammatory cytokine signaling. Acid sphingomyelinase (ASM) and neutral sphingomyelinase (NSM) are key regulatory enzymes of sphingolipid metabolism, promoting sphingomyelin hydrolysis to proinflammatory ceramide. ASM is an important early responder in inflammatory cytokine signaling. The sphingomyelinase pathway is important for inflammatory signaling in human retinal endothelial cells (HRECs), the resident vasculature affected by diabetic retinopathy. Inflammatory cytokines TNFα and IL-1β induce cellular adhesion molecule (CAM) expression and rapid increase in ASM and NSM activity in HRECs.

Previous studies have shown the importance of ASM activity in diabetic retinopathy using, e.g., ASM−/− mouse models and ASM inhibitors, such as DHA and imipramine. Such gene knockout models and anti-ASM inhibitor administration decreased retinal inflammatory markers. See Fox et al., *Diabetes* 2006; 55(12):3573-80; Opreanu et al., *Diabetes* 2011; 60(9):2370-8; Opreanu et al., *Investigative Ophthalmology & Visual Science* 2010; 51(6):3253-63; and Chakravarthy et al., *Stem Cells* 2016; 34:972-83, each incorporated by reference herein in their entirety.

However, ASM is a required enzyme, the lack or inhibition of which can lead to Niemann-Pick disease, which can be fatal. As such, ASM gene knockout and direct inhibition of the enzyme are not viable therapeutic strategies for treatment of diabetic retinopathy. In contrast, administration of the anti-ceramide antibodies and antigen-binding fragments herein provide the surprising result of selectively inhibiting inflammatory markers, neovascularization, and other symptoms of diabetic retinopathy in the eye without inducing the negative side effects associated with direct inhibition of ASM.

Additional Diseases

In some embodiments, the present compositions and methods are used in the treatment of diabetic retinopathy. In some embodiments, the present compositions and methods are used to treat diabetic macular edema. In some embodiments, the present compositions and methods are used to treat macular edema following retinal vein occlusion (RVO). In some embodiments, the present compositions and methods are used to treat myopic choroidal neovascularization (mCNV).

The present disclosure provides methods for the treatment of diseases or disorders with underlying neovascularization. Exemplary diseases and disorders of the eye include: retinal neovascularization, choroidal neovascularization, corneal neovascularization, macular degeneration, age-related macular degeneration, diabetic retinopathy, vitreous hemorrhage, retinal hemorrhage, choroiditis, neovascular glaucoma, choroid diseases, telangiectasia, retinal artery occlusion, retinal vein occlusion, chorioretinitis, epiretinal membrane, choroid neoplasms, retinopathy of prematurity, cystoid macular edema, papilledema, recurrent ischemia, eye hemorrhage, and proliferative vitreoretinopathy.

Pharmaceutical Compositions, Administration Routes, Dosages, and Dosing Schedules In some embodiments, the disclosure provides a pharmaceutical composition comprising an anti-ceramide antibody or antigen-binding fragment thereof for the treatment of diabetic retinopathy.

For administration, an antibody or fragment of the present disclosure (e.g., anti-ceramide antibodies and antigen-binding fragments thereof) may be formulated as a pharmaceutical composition. A pharmaceutical composition may comprise: (i) an anti-ceramide antibody or antigen-binding fragment thereof, and (ii) a pharmaceutically acceptable carrier, diluent or excipient. A pharmaceutical composition comprising an anti-ceramide antibody or antigen-binding fragment thereof, and/or scFv can be formulated according to known methods to prepare pharmaceutically useful compositions, whereby the therapeutic molecule is combined in a mixture with a pharmaceutically acceptable carrier, diluent or excipient. Suitable carriers, diluents or excipients are well-known to those in the art. (See, e.g., Gennaro (ed.), Remington's Pharmaceutical Sciences (Mack Publishing Company, 19th ed. 1995).) Formulations can further include one or more excipients, preservatives, solubilizers, buffering agents, albumin to prevent protein loss on vial surfaces, etc.

In some embodiments, a pharmaceutical composition may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, an intracerebral unit dosage form, an intracameral unit dosage form, a subconjunctival unit dosage form, a subtenon unit dosage form, a retrobulbar unit dosage form, a posterior juxtascleral unit dosage form, and an intravitreal unit dosage form. In some embodiments, a pharmaceutical composition may be formulated in an intravitreal dosage form. Systemic routes of administration are not expected to deliver the anti-ceramide antibodies or antigen binding fragments thereof to the eye, as the anti-ceramide antibodies or antigen binding fragments thereof are not expected to cross the blood-brain barrier.

The anti-ceramide antibodies and antigen-binding fragments thereof described herein can be administered to subjects by a variety of administration modes, including, for example, by intramuscular, subcutaneous, intravenous, intra-atrial, intra-articular, parenteral, intranasal, intrapulmonary, transdermal, intrapleural, intrathecal, oral, topical, intraocular, intracameral, subconjunctival, subtenon, retrobulbar, posterior juxtascleral, administration to the suprachoroidal space (SCS), administration to the supraciliary space, and intravitreal routes of administration.

In some embodiments, anti-ceramide antibodies and antigen-binding fragments thereof, and pharmaceutical compositions thereof disclosed herein may be administered directly to the eye by any known administration route, including topical (e.g. eye drops), local ocular, intravitreal, intracameral, subconjunctival, subtenon, retrobulbar, and posterior juxtascleral.

Many possible modes of delivery can be used, including, but not limited to intraocular application or topical application. In one embodiment the application is intraocular and includes, but is not limited to, subconjunctival injection, intracanieral injection, injection into the anterior chamber via the temporal limbus, intrastromal injection, intracorneal injection, subretinal injection, aqueous humor injection, subtenon injection or sustained delivery device, or intravitreal injection (e.g., front, mid or back vitreal injection). In one embodiment the application is topical and includes, but is not limited to eye drops to the cornea.

In some embodiments, the disclosed antibodies, antigen-binding fragments thereof, and compositions thereof are prepared for intravitreal administration. In some embodiments, the disclosed antibodies, antigen-binding fragments, and compositions thereof are administered intravitreally.

For prevention and treatment purposes, anti-ceramide antibodies and antigen-binding fragments thereof can be administered to a subject in a single bolus delivery, via continuous delivery (e.g., continuous transdermal delivery) over an extended time period, or in a repeated administration protocol (e.g., on an hourly, daily, weekly, monthly, or yearly basis).

In some embodiments, the methods provided herein comprise administering a therapeutically effective dose of an anti-ceramide antibody or antigen-binding fragment thereof. A therapeutically effective dose, dosage, or amount, as defined above, refers to the minimum amount of an anti-ceramide antibody or antigen-binding fragment thereof required to result in a particular physiological effect, e.g., prevention or amelioration of one or more symptoms of diabetic retinopathy. Determination of therapeutically effective dosages in this context is typically based on animal model studies followed up by human clinical trials and is guided by determining effective dosages and administration protocols that significantly reduce the occurrence or severity of diabetic retinopathy in model subjects. Effective doses of the compositions of the present disclosure vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Typically, dosage regimens are adjusted to provide an optimum therapeutic response, i.e., to optimize safety and efficacy.

In some embodiments, the dose of an anti-ceramide antibody or antigen-binding fragment thereof is between about 0.1 µg to 100 mg/kg or 1 µg/kg to about 50 mg/kg, or 10 µg to 5 mg/kg'. In some embodiments, an effective amount of the anti-ceramide antibody or antigen-binding fragment thereof is between about 1 µg/kg and about 20 mg/kg, between about 10 µg/kg and about 10 mg/kg, or between about 0.1 mg/kg and about 5 mg/kg. The anti-ceramide antibodies and antigen-binding fragments thereof described herein may also be administered at a dosage from about 0.001 to about 10 milligrams (mg) per kilogram (mpk) of body weight, given as a single dose or in two or more doses. For administration to a human adult patient, the therapeutically effective amount may be administered in doses in the range of 0.2 mg to 800 mg per dose, including but not limited to 0.2 mg per dose, 0.5 mg per dose, 1 mg per dose, 5 mg per dose, 10 mg per dose, 25 mg per dose, 100 mg per dose, 200 mg per dose, and 400 mg per dose, and one or more doses may be administered in a course of treatment. In some embodiments, the total daily dosage of the anti-ceramide antibodies and antigen-binding fragments thereof described herein can range from about 1 mg to about 2 g, from about 100 mg to about 1.5 g, or from about 200 mg to about 1200 mg.

In some embodiments, anti-ceramide antibodies, antigen-binding fragments thereof, or compositions comprising may be formulated at a concentration of about 0.1 mg/mL, 0.5 mg/mL, 1 mg/mL, 5 mg/mL, 10 mg/mL, 15 mg/mL, 20 mg/mL, 25 mg/mL, 30 mg/mL, 35 mg/mL, 40 mg/mL, 45 mg/mL, or 50 mg/mL. The concentration may be 0.1-1 mg/mL, 1-5 mg/mL, 5-10 mg/mL, or 10-50 mg/mL. In some embodiments, the disclosed antibodies, fragments or compositions may be administered in a dose of about 0.05 mg, 0.1 mg, 0.2 mg, 0.3 mg, 0.4 mg, 0.5 mg, 0.6 mg, 0.7 mg, 0.8 mg, 0.9 mg, or 1 mg intravitreally. The volume of the dose may be about 0.005 mL, 0.01 mL, 0.02 mL, 0.03 mL, 0.04 mL, 0.05 mL, 0.06 mL, 0.07 mL, 0.08 mL, 0.09 mL, or 0.1 mL.

The anti-ceramide antibodies and antigen-binding fragments thereof described herein can be administered at different times of the day. In one embodiment, the dose can be administered in the evening. In another embodiment, the dose can be administered in the morning. Dosages may be administered in single or multiple administrations, including, e.g., multiple weekly, bi-weekly, monthly, or yearly administrations. In some embodiments, a single dose of anti-ceramide antibody or antibody fragment is administered to a subject in need thereof. In some embodiments, a patient may receive two or more doses of anti-ceramide antibody treatments separated by a period of at least two weeks, at least three weeks, at least four weeks, at least five weeks, at least six weeks, at least seven weeks, at least eight weeks, at least one month, at least two months, at least three months, at least four months, at least five months, at least six month, at least seven months, at least eight months, at least nine months, at least ten months, at least eleven months, or at least one year. In some embodiments, two or more doses may be administered to a patient in need thereof separated by a period of about one week to about two weeks, about two weeks to about four weeks, about one month to about two months, about two months to about four months, about one month to about six months, about six months to about one year, or about one year to about two years. In some embodiments, administrations can be on an irregular basis as indicated by monitoring clinical symptoms of the disorder.

Dosage of the pharmaceutical composition comprising anti-ceramide antibodies and antigen-binding fragments thereof can be varied by the attending clinician to maintain a desired concentration at a target site. Higher or lower concentrations can be selected based on the mode of delivery. The anti-ceramide antibodies, or antigen-binding fragments thereof may be administered at any time during a subject's life. In some embodiments, administration occurs before symptoms of diabetic retinopathy develop. In such embodiments, administration may be used as a prophylactic to prevent or delay the onset of diabetic retinopathy. In some embodiments, administration occurs during early stage disease. In some embodiments, administration occurs during late stage disease.

Therapeutic Methods & Uses

In some embodiments, the present disclosure provides methods of treating, preventing, or ameliorating a symptom of an inflammatory ocular condition in a subject, comprising administering to the subject a therapeutically effective amount of an anti-ceramide antibody or an antigen-binding fragment thereof.

In some embodiments, the present disclosure provides methods of preventing and/or treating diabetic retinopathy in a subject in need thereof, comprising administering to the subject a therapeutically effective amount of anti-ceramide antibody or an anti-ceramide antibody fragment.

Previous studies have posited that the initial metabolic insult leading to inflammation and increased vascular permeability in the retina involves activation of acid sphingomyelinase (ASM), the central enzyme of sphingolipid signaling, converting sphingomyelin into ceramide. ASM−/− animals were protected from vascular degeneration in retinal ischemia-reperfusion model, and chimeras with ASM−/− bone marrow transplanted into a wild type mouse were also protected from diabetes-induced vascular damage. Several strategies have been implemented to inhibit ASM activity, including administration of docosahexaenoic acid (DHA)-rich fish oil and the tricyclic antidepressant desipramine. Both strategies show some efficacy in cell culture models. However, desipramine was not well tolerated by animals in a long-term study (See Example 8) and long-term high dose DHA treatment, although it improved retinal health in diabetic animals, caused retinal pathology in the control animals (See Example 9). Furthermore, ASM is an essential enzyme and the lack of ASM leads to neurodegenerative disease (Niemann-Pick). Therefore direct inhibition of ASM is not a viable clinical strategy in the treatment of DR. Anti-ceramide antibodies and antigen-binding fragments thereof are highly effective in binding monomeric ceramide generated on the surface of endothelial and other cells thereby preventing ASM-induced Ceramide-rich Platform formation, and consequent pro-inflammatory and apoptotic signaling, without affecting essential lysosomal ASM function.

Subjects

Subjects for treatment according to the methods disclosed herein include those who have or are at risk for developing diabetic retinopathy. Subjects who have diabetic retinopathy may have early stage or late stage disease.

In some embodiments, subjects are those who have previously received one or more treatments for diabetic retinopathy but failed to respond to the previous treatment. In such embodiments, a "failure to respond" indicates that the previous treatment failed to ameliorate and/or improve one or more symptoms of diabetic retinopathy. In some embodiments, the previous therapy may have failed to produce an improvement in vision or in retinal vascular health. In some embodiments, the previous therapy may have shown some results, but may not have achieved the desired performance or may have stopped showing efficacy after some period of time.

Existing treatments for diabetic retinopathy include therapeutic procedures, such as vitrectomy and laser surgery, and therapeutic agents, such as steroids and anti-vascular endothelial growth factor (VEGF) therapy. In some embodiments, the subject may have partially responded to a previous diabetic retinopathy treatment: i.e., one or more symptoms of diabetic retinopathy were not sufficiently ameliorated and/or the effects of the previous treatment were not sufficiently durable.

In some embodiments, the subject previously received an anti-VEGF treatment and failed to respond. In some embodiments, the anti-VEGF treatment is selected from Eylea® (aflibercept), Avastin® (bevacizumab), or Lucentis® treatment (ranibizumab).

Treatment Readouts

Treatment and/or prevention of diabetic retinopathy can be measured by a variety of means. In some embodiments, treatment or prevention comprises treating or preventing one or more of apoptosis, inflammation, acellular capillary formation, neovascularization, retinal endothelial cell death, retinal vascular permeability, ischemic reperfusion injury, and occludin disruption in diabetic retinopathy in a subject in need thereof. The method comprises administration of an effective amount of an anti-ceramide antibody, or antigen-binding fragment thereof, before the onset of diabetic retinopathy in a diabetic patient or after the onset of diabetic retinopathy in a diabetic patient.

Provided are methods of treating diabetic retinopathy with an anti-ceramide antibody or antigen-binding fragment thereof. Efficacy of such treatment may be characterized, evaluated, measured, and/or monitored based on several parameters.

In some embodiments, the methods provided herein result in decreased apoptosis and/or endothelial cell death within the eye. Cell death may be monitored according to known methods. Illustrative methods for detecting cell death include nuclear staining techniques such as propidium iodide, Hoechst-33342, 4', 6-diamidino-2-phenylindole (DAPI), Acridine orange-Ethidium bromide staining, and the like. Nonnuclear staining techniques include Annexin-V staining.

In some embodiments, the methods provided herein prevent ischemia-reperfusion (IR) injury. Additional methods for detecting IR injury include fluorescein analysis, fluorescent zinc 2,2'-dipicolylamine coordination complex PSVue®794, 99mTc glucarate, and electroretinography.

In some embodiments, the methods provided herein reduce levels of inflammatory cytokines, such as TNFα, IL-1β, IL-6, or MCP1. Cytokine levels may be monitored via enzyme-linked immunosorbant assay (ELISA), Luminex, Cytokine Bead Array, Proteo Plex, FAST Quant, and the like.

In some embodiments, methods provided herein reduce retinal vascular permeability, retinal neovascularization, or other symptoms of retinal health. In some embodiments, methods provided herein may prevent typical symptoms of diabetic retinopathy in the retinal vasculature or may prevent further deterioration. Vascular permeability and other measures of retinal vascular health may be measured by, e.g., fluorescein angiography.

In some embodiments, the methods provided herein improve one or more vision parameters or prevent the decline of one or more vision parameters. Vision parameters include: poor night vision, blurred vision, floating spots, black spots or flashing lights in the vision field, fluctuating vision, impaired color vision, dark or empty areas in your vision, vision loss, sudden severe painless vision loss. In some embodiments, subjects receiving treatment according to the methods provided herein may experience one or more of the following effects: improved vision, reduced vision loss, improved night vision, improved low light vision, improved reading ability, improved peripheral vision, reduced spots in the vision field, reduced flashing lights in the vision field, reduced pain, and improved eye appearance. Many of these parameters may be monitored through routine eye examination.

In some embodiments, the methods provided herein prevent diabetic retinopathy. The methods may be administered to patients at risk for developing diabetic retinopathy. In such subjects, prevention of diabetic retinopathy may be monitored by maintenance of vision or by lack of typical hallmarks of diabetic retinopathy. For example, subjects to whom anti-ceramide antibodies or antigen-binding fragments thereof have been administered prophylactically may not experience or may experience a reduced incidence of one or more of the following symptoms: microaneurysms, hemorrhages, intraretinal microvascular abnormalities, venous beading, cotton wool spots, the formation of new blood vessels (neovascularization) elsewhere and on the optic nerve, fibrous proliferation elsewhere and on the optic nerve, preretinal and vitreous hemorrhage, retinal detachment due to scar tissue formation, glaucoma, poor night vision, blurred vision, floating spots, black spots or flashing lights in the vision field, fluctuating vision, impaired color vision, dark or empty areas in your vision, vision loss, sudden severe painless vision loss, traction retinal detachment, macular edema, venous dilation, and intraretinal microvascular abnormalities.

In some embodiments, the methods provided herein prevent or reduce macular edema. Macular edema may be seen on slit-lamp biomicroscopy as elevation and blurring of retinal layers.

In some embodiments, the methods provided herein delay the onset of diabetic retinopathy. Accordingly, the disclosed methods may be used to delay the average onset of diabetic retinopathy to greater than 5 years, greater than 10 years, greater than 11 years, greater than 12 years, greater than 13 years, greater than 14 years, greater than 15 years, greater than 16 years, greater than 17 years, greater than 18 years, greater than 19 years, or greater than 20 years after initial diabetes diagnosis.

In some embodiments, the disclosed methods may be used to reduce, ameliorate, lessen the severity of, or reverse one or more symptoms of diabetic retinopathy. In some embodiments, methods of treating diabetic retinopathy with anti-ceramide antibodies or antigen-binding fragments thereof may reduce, ameliorate, lessen the severity of, or reverse one or more of the following symptoms: microaneurysms, hemorrhages, intraretinal microvascular abnormalities, venous beading, cotton wool spots, the formation of new blood vessels (neovascularization) elsewhere and on the optic nerve, fibrous proliferation elsewhere and on the optic nerve, preretinal and vitreous hemorrhage, retinal detachment due to scar tissue formation, loss of vision, glaucoma, poor night vision, blurred vision, floating spots, black spots or flashing lights in the vision field, sudden severe painless vision loss, traction retinal detachment, macular edema, venous dilation, and intraretinal microvascular abnormalities.

In some embodiments, the disclosed methods of treating diabetic retinopathy affect one or more parameters of the retinal vasculature, including, but not limited to: permeability, NFkB levels, inflammatory marker levels, apoptosis incidence, sphingolipid metabolism, and reendothelialization. In some embodiments, a method of treating diabetic retinopathy disclosed herein decreases retinal vascular permeability. Retinal vascular permeability may be monitored via fluorescence, tracer dyes, optical exam, and the like. In some embodiments, a method of treating diabetic retinopathy disclosed herein decreases NFkB and/or other inflammatory marker levels in the retinal vasculature. As disclosed above, inflammatory cytokine levels may be measured through conventional means (e.g., ELISA). In some embodiments, a method of treating diabetic retinopathy disclosed herein decreases the incidence of apoptosis in the retinal vasculature. As disclosed above, apoptosis may be measured using conventional means, e.g., nuclear and nonnuclear staining techniques. In some embodiments, a method of treating diabetic retinopathy disclosed herein inhibits or downregulates sphingolipid metabolism. In some embodiments, a method of treating diabetic retinopathy disclosed herein may increase healthy tissue reendothelialization.

EXAMPLES

Example 1: Anti-Ceramide scFv Inhibits I/R Inflammation and Retinal Vascular Permeability in a Murine Model of Diabetic Retinopathy The murine ischemia-reperfusion (I/R) model of diabetic retinopathy was employed to simulate the damaging effects of diabetic retinopathy on the retinal vasculature, e.g., as illustrated in FIG. 1.

Retinal ischemia-reperfusion (I/R): Each mouse had one I/R eye and one undamaged, control eye. Retinal I/R was created by temporal increase in intraocular pressure (IOP) to 90 mmHg, as follows. Male C57BL/6J mice weighing 25 to 30 g were anesthetized. The anterior chamber of one eye was cannulated with a 30-gauge needle attached to a line infusing normal saline. IOP was measured by a handheld tonometer (TONO Pen; Medtronic Solan, Jacksonville, Fla.) in mouse eyes, and pressure in the eye was regulated to 80 to 90 mm Hg with a pressure infuser (Infu-surg; Ethox Corp., Buffalo, N.Y.). The other eye of the same animal was set up as a control. The duration of ischemia was 90 minutes for mice. After ischemia, the needle was withdrawn, IOP was normalized, and reflow of the retinal circulation was documented visually. Animals were killed at different times after I/R injury. The retinas were isolated either 2 or 7 days after retinal I/R.

Vehicle control or anti-ceramide scFv administration: Twenty-four hours prior to I/R, control mice received vehicle (phosphate-buffered saline) injections and test mice received an intravitreal injection of 1 µL of anti-ceramide scFv 6B5 at 1.73 mg/mL.

Inflammatory cytokine levels: 48 hours after I/R, measurements were taken of inflammatory cytokine expression levels for TNFα, IL-1β, IL6, ICAM-1, VCAM-1, and MCP1 using quantitative PCR analysis.

Additional measurements that may be taken: In comparable experiments using this model, measurements are taken of permeability, inflammatory markers, and sphingolipid metabolism after 48 hours, and after 7 days, measurements are taken of apoptosis, acellular capillaries, and sphingolipid metabolism, as illustrated in FIG. 2.

Retinal vascular permeability: Retina were isolated 48 hours after I/R. Briefly, mice were injected with FITC-albumin (0.5 mg in 100 µL PBS) (Sigma-Aldrich, St. Louis, Mo.). After two hours, blood was collected from each mouse and centrifuged to obtain plasma; the animal was perfused with 1% formaldehyde and enucleated. Retinas were removed, flat-mounted with four slits and kept on glass slides with Fluoromount mounting medium (Sigma-Aldrich, St. Louis, Mo.). Images were acquired using an Olympus FluoView 1000 scanning laser confocal microscope and at least 5 different view areas were selected to collect images for each sample. Retinas were disrupted mechanically and cleared by centrifugation. FITC-albumin in supernatant was quantified using spectrofluorometer and normalized to plasma fluorescence (Kielczewski et al., 2011).

Results

Figure 2A:
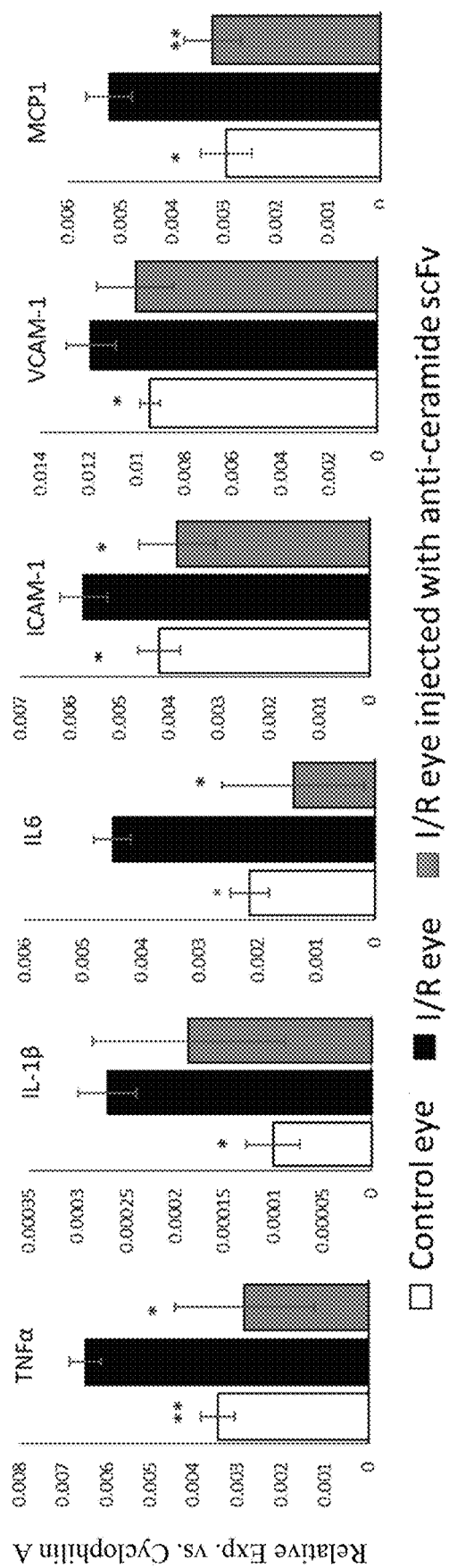
FIG. 2A-FIG. 2B show the results of intravitreal anti-ceramide scFv administration in mice with retinal ischemia-reperfusion (I/R) injury in a murine model of diabetic retinopathy.
Figure 2B:
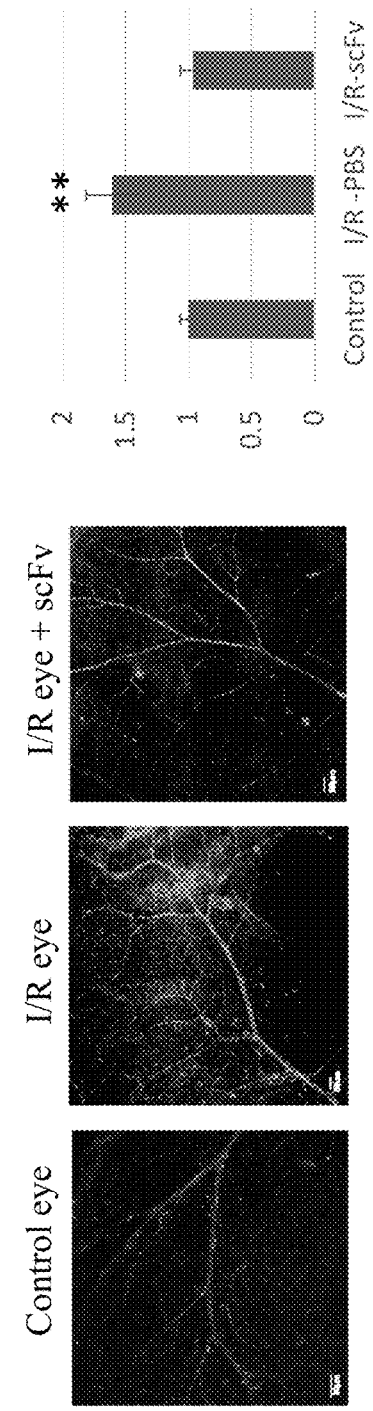

As shown in FIG. 2A, cytokine expression in the anti-ceramide treated I/R eyes was lower than in untreated I/R eyes for each of the tested cytokines (TNFα, IL-1β, IL6, ICAM-1, VCAM-1, and MCP1). The decrease observed in TNFα, IL6, ICAM-1, and MCP1 was statistically significant. FIG. 2B reveals a clear difference in retinal vascular permeability as demonstrated via fluorescence microscopy images and quantitative analysis. Permeability was significantly higher in untreated I/R eyes than in either control eyes or anti-ceramide treated I/R eyes.

This example demonstrates that a single intravitreal injection of anti-ceramide scFv at the onset of diabetes improves outcome of eventual diabetic retinopathy by preventing endothelial cell loss and subsequent damage to the retina.

Figure 3:
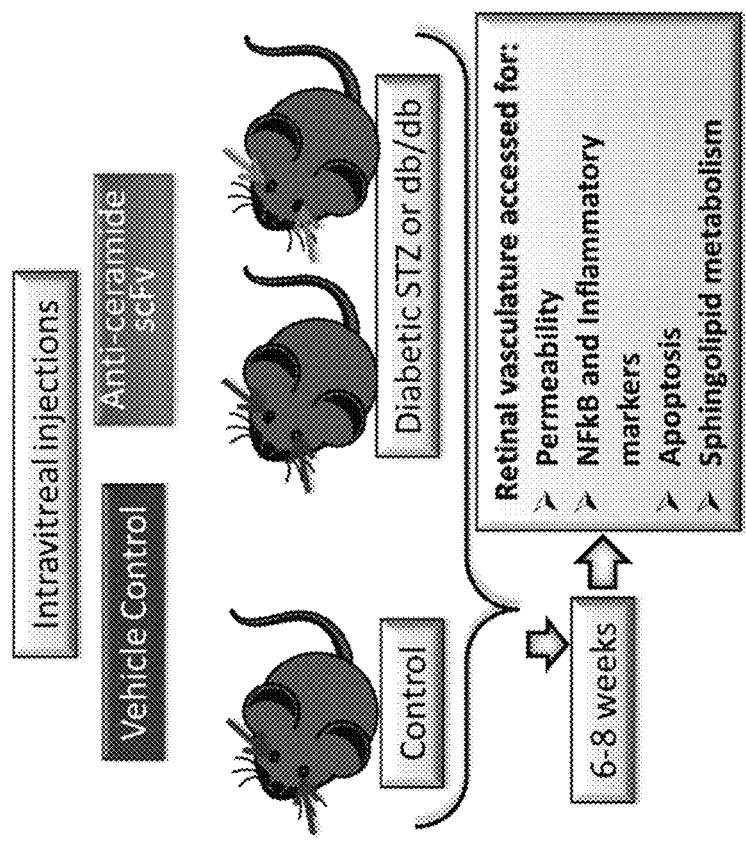
FIG. 3 shows an exemplary experimental design for measuring the effect of intravitreal anti-ceramide scFv administration in a murine model of diabetes.

Example 2: Efficacy of Anti-Ceramide scFv Administration in a Rat Model of Diabetic Retinopathy The STZ-induced model of diabetic retinopathy was employed in rats to simulate the damaging effects of diabetic retinopathy on the retinal vasculature, e.g., as illustrated in FIG. 3.

Animals and induction of STZ-induced diabetes: Male Sprague-Dawley rats weighing 237-283 g were made diabetic with a single intraperitoneal injection of 65 mg streptozotocin (STZ) per kg body wt. Rats were maintained on Harlan-Teklad laboratory diet (no. 8,640) and water ad libitum. Body weight gains and blood glucose for the control and STZ-induced diabetic groups were monitored biweekly.

Vehicle control or anti-ceramide scFv administration: after the confirmation of diabetes (hyperglycemia above 250 mg/dL, 7-10 days after STZ injection), diabetic control rats received vehicle PBS injections and diabetic test rats received an intravitreal injection of 2 µL of anti-ceramide scFv 6B5 at 1.73 mg/mL. Non-diabetic control rats also received an injection of either vehicle control or anti-ceramide scFv.

Retina vascular permeability analysis: Retina were isolated 48 hours after I/R. Briefly, mice were injected with FITC-albumin (0.5 mg in 100 µL PBS) (Sigma-Aldrich, St. Louis, Mo.). After two hours, blood was collected from each mouse and centrifuged to obtain plasma; the animal was perfused with 1% formaldehyde and enucleated. Retinas were removed, flat-mounted with four slits and kept on glass slides with Fluoromount mounting medium (Sigma-Aldrich, St. Louis, Mo.). Images were acquired using an Olympus FluoView 1000 scanning laser confocal microscope and at least 5 different view areas were selected to collect images for each sample. Retinas were disrupted mechanically and cleared by centrifugation. FITC-albumin in supernatant was quantified using spectrofluorometer and normalized to plasma fluorescence (Kielczewski et al., 2011).

Additional measurements: In comparable experiments, the experiment is carried out in a murine model or the diabetic model is db/db leptin deficiency, as shown in FIG. 3. In addition, 6-8 weeks after induction of diabetes in the STZ-induced model, the retinal vasculature of each animal is assessed for permeability, NFkB and inflammatory markers, apoptosis, and sphingolipid metabolism, as demonstrated in FIG. 3.

Results

Figure 4:
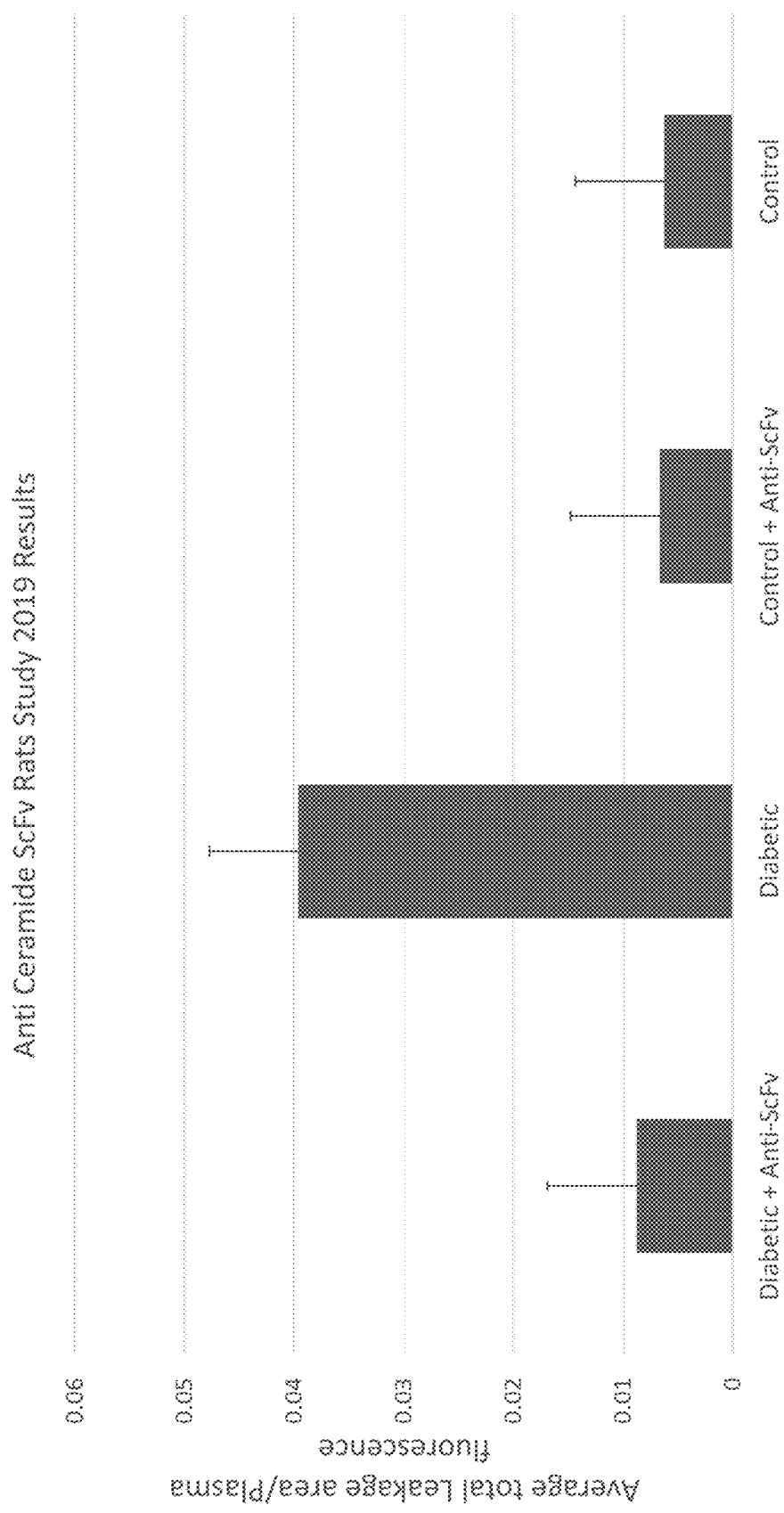
FIG. 4 shows the results of anti-ceramide scFv administration in diabetic rats.

The results contained in FIG. 4 demonstrate that diabetic rats receiving an intravitreal dose of anti-ceramide scFv did not develop the vascular leakage indicative of diabetic retinopathy, thus demonstrating that a single intravitreal injection of an anti-ceramide scFv is sufficient to eliminate hyperglycemia-induced Diabetic retinopathy in a rat model of this condition.

Figure 5:
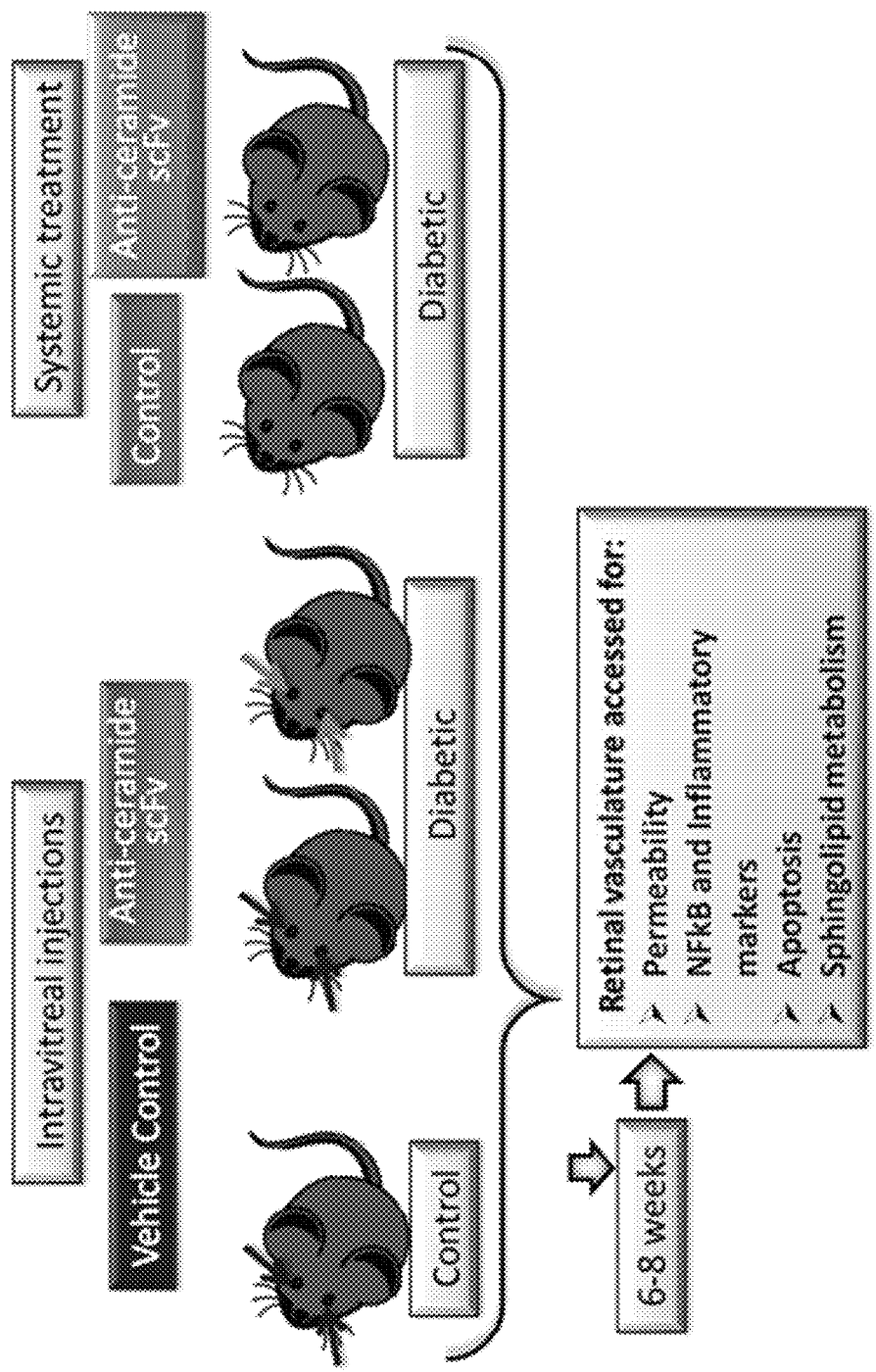
FIG. 5 shows an exemplary experimental design for comparing the effects of intravitreal and systemic anti-ceramide scFv administration in a murine model of diabetic retinopathy.

Example 3: Intravitreal Versus Systemic Administration of Anti-Ceramide scFv for Treating Diabetes-Induced Pro-Inflammatory Changes in DR Experiments are performed to compare the effect of intravitreal anti-ceramide treatment versus systemic anti-ceramide treatment on diabetes-induced pro-inflammatory changes in a DR mouse model. STZ-induced type 1 diabetic mice receive a single intravitreal or systemic (intravenous) anti-ceramide treatment with 6B5 scFv at the onset of diabetes. 6-8 weeks after STZ administration, control, diabetic and anti-ceramide-treated diabetic animals are sacrificed. From each animal, retinas are isolated; inflammatory cytokines, growth factors and adhesion molecules are profiled; and endothelial ASM expression and activity is measured in the retinas. These measurements are performed with qPCR, Western blot, ESI-MS/MS, fluorescent microscopy and immunogold electron microscopy experiments. An exemplary experimental protocol is illustrated in FIG. 5.

It is expected that a single intravitreal injection of anti-ceramide scFv will have a greater therapeutic effect on the development of DR. Additional experiments are performed to assess the ability of a single intravitreal dose of anti-ceramide antibody or antigen-binding fragment thereof to treat existing DR pathologies.

Example 4: Intravitreal Versus Systemic Administration of Anti-Ceramide scFv for Treating DR Vascular Dysfunction Experiments are performed to compare the effect of intravitreal versus systemic anti-ceramide treatment on retinal vascular permeability in a DR mouse model. For this example, the effect of 6B5 anti-ceramide scFv administration on diabetes-induced retinal vascular damage is measured. To assess initial blood-retinal barrier breakdown, mice receive a single intravitreal or systemic (intravenous) anti-ceramide scFv treatment at the onset of diabetes. 6-8 weeks after induction of diabetes, retinal vascular permeability is assessed using fluorescein as described in Example 2. An exemplary experimental protocol is illustrated in FIG. 5.

It is expected that a single intravitreal injection of scFv will have a greater therapeutic effect on DR vascular dysfunction. Additional experiments are performed to assess the ability of a single intravitreal dose of anti-ceramide antibody or antigen-binding fragment thereof to treat existing DR pathologies.

Figure 6:
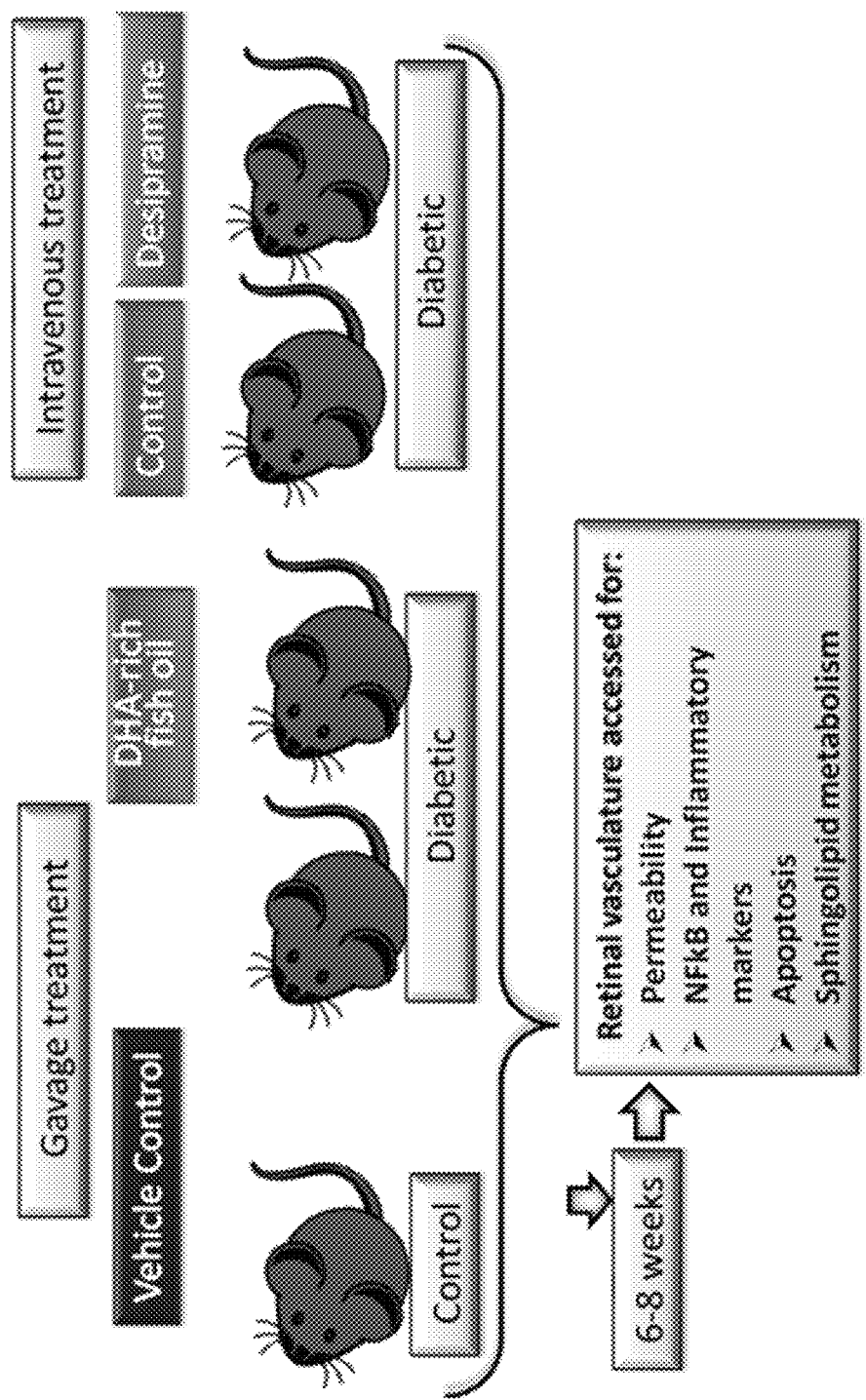
FIG. 6 shows an exemplary experimental design for comparing the effects of anti-ceramide scFv administration and DHA administration in a murine model of diabetic retinopathy.

Example 5: Anti-Ceramide scFv Versus DHA or Desipramine for Reducing Pro-Inflammatory Changes in DR Experiments are performed to compare the effects of single anti-ceramide intravitreal or systemic scFv treatment to the effects of single DHA-rich fish oil or desipramine treatment on diabetes-induced pro-inflammatory changes in a DR mouse model. STZ-induced type 1 diabetic mice receive a single dose of DHA-rich fish oil by gavage, a single intravenous injection of desipramine, a single intravitreal injection of anti-ceramide scFv, or a systemic injection of anti-ceramide scFv at onset of diabetes. 6-8 weeks after STZ induction of diabetes, the animals are sacrificed and their retinas are isolated. Inflammatory cytokines, growth factors and adhesion molecules are profiled. Endothelial ASM expression and activity are measured. These measurements are performed in a series of qPCR, Western blot, ESI-MS/MS, fluorescent microscopy and immunogold electron microscopy experiments as described in Example 3. An exemplary experimental protocol is illustrated in FIG. 6.

It is expected that a single intravitreal injection of anti-ceramide scFv will have a greater therapeutic effect on the development of DR. Additional experiments are performed to assess the ability of a single intravitreal dose of anti-ceramide antibody or antigen-binding fragment thereof to treat existing DR pathologies.

Example 6: Anti-Ceramide scFv Administration Versus DHA or Desipramine for Treating DR Vascular Dysfunction Experiments are performed to compare the effect of single intravitreal or systemic anti-ceramide scFv treatment vs. single DHA-rich fish oil or desipramine treatment on retinal vascular permeability in a DR mouse model. STZ-induced type 1 diabetic mice receive a single dose of DHA-rich fish oil by gavage, a single intravenous injection of desipramine, a single intravitreal injection of anti-ceramide scFv, or a systemic injection of anti-ceramide scFv at onset of diabetes. 6-8 weeks after induction of diabetes, retinal vascular permeability is assessed using fluorescein as described in Example 4. An example experimental protocol is illustrated in FIG. 6.

It is expected that a single intravitreal injection of scFv will have a greater therapeutic effect on DR vascular dysfunction. Additional experiments are performed to assess the ability of a single intravitreal dose of anti-ceramide antibody or antigen-binding fragment thereof to treat existing DR pathologies.

Example 7: Anti-Ceramide scFv Administration Inhibits Stress-Induced Apoptosis Experiments are performed to demonstrate that anti-ceramide scFv is effective in human retinal endothelial cells (HREC) in culture to inhibit stress-induced apoptosis under conditions where anti-angiogenic drugs are ineffective. The mechanism of DR therapy with anti-ceramide scFv and anti-angiogenic drugs is distinct from previously characterized mechanisms. Without being limited by theory, it is believed that there is ongoing death and remodeling in diabetes that cannot be addressed by anti-VEGF treatment, but which does respond to anti-ceramide. Hence, while anti-VEGF may only prevent neo-angiogenesis, anti-ceramide antibody administration may prevent ongoing endothelial cell death, enhancing vascular recovery, and preventing hypoxia and ensuing neo-angiogenesis. To test whether anti-ceramide scFv will work in vitro under conditions where anti-angiogenics are ineffective, HRECs are subjected to diverse stress conditions that induce ASM/ceramide-mediated apoptotic death (e.g., exposure to IL-1β and TNFα cytokines or $H_2O_2$). The HRECs are treated with either anti-VEGF inhibitors (anti VEGFR2 DC101 Ab or the VEGFR TK inhibitor Sorafenib) or anti-ceramide antibodies.

It is expected that anti-ceramide scFv administration will have a greater therapeutic effect on inhibiting endothelial cell death.

Example 8: Desipramine Treatment of Diabetic Mice

Diabetes was induced in male C57BL/6J mice (20-25 g) by intraperitoneal injections of SZT (65 mg/kg) on five consecutive days. Control animals received citric acid vehicle injections (pH 4.5). Two weeks after the last injection, blood glucose was measured from a drop of blood collected from the pedal dorsal vein. Diabetes was confirmed by blood glucose levels ≥300 mg/dL. Weight loss, polyuria, water and food consumption were monitored daily. On the first day that diabetes was confirmed, desipramine was added to the water for the beginning of treatment, ~2 weeks after the first SZT injection. Desipramine treatment had no effect on control animals. However, diabetic animals became dehydrated and lost more than 25% of their weight within 2-4 days at which point the experiment had to be terminated according to IACUC humane animal use regulations.

As diabetic animals have polydipsia and polyurea, desipramine in the water could have affected the drinking pattern causing dehydration. Therefore, the experiment was repeated using IP injections of 2 mg/ml desipramine for a dose of 20 mg/kg. As with the desipramine in the water treatment, the control animals tolerated the drug well. However, diabetic animals displayed abnormal tremors, became weak, stopped grooming, eating, and drinking, and lost more than 25% of their weight within 5-7 days of daily injections, at which point the experiment had to be terminated according to IACUC humane animal use regulations.

Example 9: DHA Treatment of Wild-Type Mice

Figure 7:
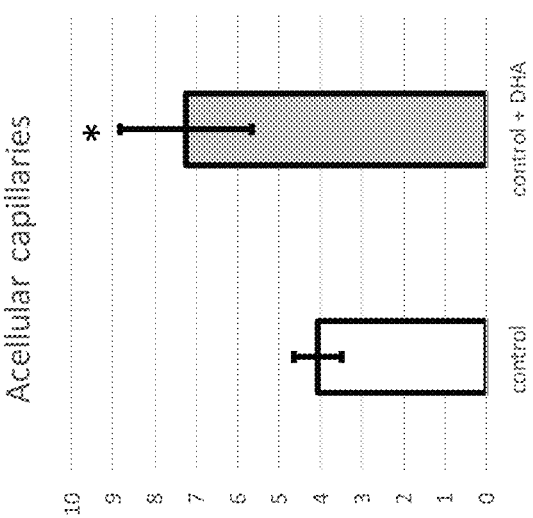
FIG. 7 shows acellular capillaries in DHA-treated control mice.

Male Sprague-Dawley rats (237-283) were fed with either control AIN-93M purified rodent diet with 10% caloric intake as soybean oil containing 50.8% linoleic acid from Dyets Inc. (Bethlehem, Pa.), or DHA-rich fish oil diet in which half of the soybean oil, or 5% caloric intake was replaced with Menhaden oil containing 10.26% DHA and 14.16% EPA. After 9 months on the diet, rat retinal vasculature was isolated by trypsin digestion and acellular capillaries were systematically counted in the mid-retina by two independent investigators. As shown in FIG. 7, DHA-rich fish oil treatment was detrimental in the control animals, causing the development of acellular capillaries.

Although health benefits of fish oil as triglyceride lowering agent are well accepted, the dose required for retinal effects was ~5% caloric intake, corresponding to ~12 g of fish oil per day, 3 times higher than recommended in humans. The high dose of DHA in humans, and especially in diabetes is associated with a number of well-described side effects, including higher blood glucose levels, excessive bleeding, reduced wound healing, frequent infections, gastrointestinal problems and weight gain. Due to these concerns, DHA is not recommended for diabetic complications.

FURTHER NUMBERED EMBODIMENTS

Further embodiments of the instant invention are provided in the numbered embodiments below:

Embodiment 1. A method of treating or preventing diabetic retinopathy in a subject in need thereof comprising ocularly administering an anti-ceramide antibody or antigen-binding fragment thereof to the subject.

Embodiment 2. The method of Embodiment 1, wherein the anti-ceramide antibody or antigen-binding fragment thereof is a single-chain variable fragment (scFv).

Embodiment 3. The method of Embodiment 1 or 2, wherein the ocular administration is selected from the group consisting of topical administration, intraocular administration, subconjunctival administration, intracameral administration, injection into the anterior chamber via the temporal limbus, intrastromal administration, intracorneal administration, subretinal administration, aqueous humor injection, subtenon administration, administration to the suprachoroidal space (SCS), administration to the supraciliary space, and intravitreal administration.

Embodiment 4. The method of any one of Embodiments 1-3, wherein the administration is intravitreal administration.

Embodiment 5. The method of any one of Embodiments 1-4, wherein the subject has received a prior treatment for diabetic retinopathy.

Embodiment 6. The method of Embodiment 5, wherein the subject failed to respond to the prior treatment for diabetic retinopathy.

Embodiment 7. The method of Embodiment 5 or 6, wherein the prior treatment is a therapeutic procedure selected from a vitrectomy and laser surgery, or a therapeutic agent selected from a steroid and an anti-vascular endothelial growth factor (VEGF) therapy.

Embodiment 8. The method of Embodiment 7, wherein the anti-VEGF therapy is an anti-VEGF antibody selected from the group consisting of bevacizumab, ranibizumab, and aflibercept.

Embodiment 9. The method of any one of Embodiments 1-8, wherein the anti-ceramide antibody or antigen-binding fragment thereof is administered as a single dose.

Embodiment 10. The method of any one of Embodiments 1-8, wherein the anti-ceramide antibody or antigen-binding fragment thereof is administered in two or more doses separated by at least two weeks, at least three weeks, or at least four weeks.

Embodiment 11. The method of any one of Embodiments 1-8, wherein the anti-ceramide antibody or antigen-binding fragment thereof is administered in two or more doses separated by about two weeks to about four weeks.

Embodiment 12. The method of any one of Embodiments 1-8, wherein the anti-ceramide antibody or antigen-binding fragment thereof is administered in two or more doses separated by at least one month, at least two months, at least three months, at least four months, at least five months, at least six months, at least seven months, at least eight months, at least nine months, at least ten months, or at least eleven months.

Embodiment 13. The method of any one of Embodiments 1-8, wherein the anti-ceramide antibody or antigen-binding fragment thereof is administered in two or more doses separated by about one month to about six months.

Embodiment 14. The method of any one of Embodiments 1-8, wherein the anti-ceramide antibody or antigen-binding fragment thereof is administered in two or more doses separated by at least one year.

Embodiment 15. The method of any one of Embodiments 1-14, wherein the anti-ceramide antibody or antigen-binding fragment thereof is administered before the onset of one or more symptoms of diabetic retinopathy.

Embodiment 16. The method of any one of Embodiments 1-14, wherein the anti-ceramide antibody or antigen-binding fragment thereof is administered after the onset of one or more symptoms of diabetic retinopathy.

Embodiment 17. The method of any one of Embodiments 1-14, wherein the anti-ceramide antibody or antigen-binding fragment thereof is administered during a non-proliferative stage of diabetic retinopathy.

Embodiment 18. The method of Embodiment 17, wherein the anti-ceramide antibody or antigen-binding fragment thereof is administered during a proliferative stage of diabetic retinopathy.

Embodiment 19. A method of treating or preventing diabetic retinopathy in a subject in need thereof comprising administering an anti-ceramide antibody or antigen-binding fragment thereof to the subject, wherein the subject has received a prior treatment for diabetic retinopathy.

Embodiment 20. The method of Embodiment 19, wherein the subject failed to respond to the prior treatment for diabetic retinopathy.

Embodiment 21. The method of Embodiment 19 or 20, wherein the anti-ceramide antibody or antigen-binding fragment thereof is a single-chain variable fragment (scFv).

Embodiment 22. The method of any one of Embodiments 19-21, wherein the administration is ocular administration.

Embodiment 23. The method of Embodiment 22, wherein the ocular administration is selected from the group consisting of topical administration, intraocular administration, subconjunctival administration, intracameral administration, injection into the anterior chamber via the temporal limbus, intrastromal administration, intracorneal administration, subretinal administration, aqueous humor injection, subtenon administration, administration to the suprachoroidal space (SCS), administration to the supraciliary space, and intravitreal administration.

Embodiment 24. The method of Embodiment 22 or 23, wherein the ocular administration is intravitreal administration.

Embodiment 25. The method of any one of Embodiments 19-24, wherein the prior treatment was a vitrectomy, laser surgery, a steroid, and/or an anti-vascular endothelial growth factor (VEGF) therapy.

Embodiment 26. The method of Embodiment 25, wherein the anti-VEGF therapy is an anti-VEGF antibody selected from the group consisting of bevacizumab, ranibizumab, and aflibercept.

Embodiment 27. The method of any one of Embodiments 19-26, wherein the anti-ceramide antibody or antigen-binding fragment thereof is administered as a single dose.

Embodiment 28. The method of any one of Embodiments 19-26, wherein the anti-ceramide antibody or antigen-binding fragment thereof is administered in two or more doses separated by at least two weeks, at least three weeks, or at least four weeks.

Embodiment 29. The method of any one of Embodiments 19-26, wherein the anti-ceramide antibody or antigen-binding fragment thereof is administered in two or more doses separated by about two weeks to about four weeks.

Embodiment 30. The method of any one of Embodiments 19-26, wherein the anti-ceramide antibody or antigen-binding fragment thereof is administered in two or more doses separated by at least one month, at least two months, at least three months, at least four months, at least five months, at least six months, at least seven months, at least eight months, at least nine months, at least ten months, or at least eleven months.

Embodiment 31. The method of any one of Embodiments 19-26, wherein the anti-ceramide antibody or antigen-binding fragment thereof is administered in two or more doses separated by about one month to about six months.

Embodiment 32. The method of any one of Embodiments 19-26, wherein the anti-ceramide antibody or antigen-binding fragment thereof is administered in two or more doses separated by at least one year.

Embodiment 33. The method of any one of Embodiments 19-32, wherein the anti-ceramide antibody or antigen-binding fragment thereof is administered before the onset of one or more symptoms of diabetic retinopathy.

Embodiment 34. The method of any one of Embodiments 19-32, wherein the anti-ceramide antibody or antigen-binding fragment thereof is administered after the onset of one or more symptoms of diabetic retinopathy.

Embodiment 35. The method of any one of Embodiments 19-32, wherein the anti-ceramide antibody or antigen-binding fragment thereof is administered during a non-proliferative stage of diabetic retinopathy.

Embodiment 36. The method of any one of Embodiments 19-32, wherein the anti-ceramide antibody or antigen-binding fragment thereof is administered during a proliferative stage of diabetic retinopathy.

Embodiment 37. A method of treating or preventing diabetic retinopathy in a subject comprising administering a single dose of an anti-ceramide antibody or antigen-binding fragment thereof to the subject.

Embodiment 38. A method of treating or preventing diabetic retinopathy in a subject comprising administering two or more doses of an anti-ceramide antibody or antigen-binding fragment thereof to the subject, wherein the two or more doses are separated by at least two weeks.

Embodiment 39. The method of Embodiment 38, wherein the anti-ceramide antibody or antigen-binding fragment thereof is administered in two or more doses separated by at least two weeks, at least three weeks, or at least four weeks.

Embodiment 40. The method of Embodiment 38, wherein the anti-ceramide antibody or antigen-binding fragment thereof is administered in two or more doses separated by about two weeks to about four weeks.

Embodiment 41. The method of Embodiment 38, wherein the anti-ceramide antibody or antigen-binding fragment thereof is administered in two or more doses separated by at least one month, at least two months, at least three months, at least four months, at least five months, at least six months, at least seven months, at least eight months, at least nine months, at least ten months, or at least eleven months.

Embodiment 42. The method of Embodiment 38, wherein the anti-ceramide antibody or antigen-binding fragment thereof is administered in two or more doses separated by about one month to about six months.

Embodiment 43. The method of Embodiment 38, wherein the anti-ceramide antibody or antigen-binding fragment thereof is administered in two or more doses separated by at least one year.

Embodiment 44. The method of any one of Embodiments 37-43, wherein the anti-ceramide antibody or antigen-binding fragment thereof is a single-chain variable fragment (scFv).

Embodiment 45. The method of any one of Embodiments 37-44, wherein the administration is ocular administration.

Embodiment 46. The method of Embodiment 45, wherein the ocular administration is selected from the group consisting of topical administration, intraocular administration, subconjunctival administration, intracameral administration, injection into the anterior chamber via the temporal limbus, intrastromal administration, intracorneal administration, subretinal administration, aqueous humor injection, sub-tenon administration, administration to the suprachoroidal space (SCS), administration to the supraciliary space, or intravitreal administration.

Embodiment 47. The method of Embodiment 45 or 46, wherein the ocular administration is intravitreal administration.

Embodiment 48. The method of any one of Embodiments 37-47, wherein the subject has received a prior treatment for diabetic retinopathy.

Embodiment 49. The method of Embodiment 48, wherein the subject failed to respond to the prior treatment for diabetic retinopathy.

Embodiment 50. The method of Embodiment 48 or 49, wherein the prior treatment was a vitrectomy, laser surgery, a steroid, and/or an anti-vascular endothelial growth factor (VEGF) therapy.

Embodiment 51. The method of Embodiment 50, wherein the anti-VEGF therapy is an anti-VEGF antibody selected from the group consisting of bevacizumab, ranibizumab, and aflibercept.

Embodiment 52. The method of any one of Embodiments 37-51, wherein the anti-ceramide antibody or antigen-binding fragment thereof is administered before the onset of one or more symptoms of diabetic retinopathy.

Embodiment 53. The method of any one of Embodiments 37-51, wherein the anti-ceramide antibody or antigen-binding fragment thereof is administered after the onset of one or more symptoms of diabetic retinopathy.

Embodiment 54. The method of any one of Embodiments 37-51, wherein the anti-ceramide antibody or antigen-binding fragment thereof is administered during a non-proliferative stage of diabetic retinopathy.

Embodiment 55. The method of any one of Embodiments 37-51, wherein the anti-ceramide antibody or antigen-binding fragment thereof is administered during a proliferative stage of diabetic retinopathy.

Embodiment 56. A method of treating an ocular inflammatory disease comprising ocularly administering an anti-ceramide antibody or antigen-binding fragment thereof.

Embodiment 57. The method of Embodiment 56, wherein the anti-ceramide antibody or antigen-binding fragment thereof is a single-chain variable fragment (scFv).

Embodiment 58. The method of Embodiment 56 or 57, wherein the ocular administration is selected from the group consisting of topical administration, intraocular administration, subconjunctival administration, intracameral administration, injection into the anterior chamber via the temporal limbus, intrastromal administration, intracorneal administration, subretinal administration, aqueous humor injection, subtenon administration, administration to the suprachoroidal space (SCS), administration to the supraciliary space, or intravitreal administration.

Embodiment 59. The method of any one of Embodiments 56-58, wherein the ocular inflammatory disease is selected from the group consisting of retinal neovascularization, choroidal neovascularization, corneal neovascularization, macular degeneration, age-related macular degeneration, diabetic retinopathy, vitreous hemorrhage, retinal hemorrhage, choroiditis, neovascular glaucoma, choroid diseases, telangiectasia, retinal artery occlusion, retinal vein occlusion, chorioretinitis, epiretinal membrane, choroid neoplasms, retinopathy of prematurity, cystoid macular edema, papilledema, recurrent ischemia, eye hemorrhage, and proliferative vitreoretinopathy.

Embodiment 60. The method of any one of Embodiments 56-59, wherein the ocular administration is intravitreal administration.

Embodiment 61. The method of any one of Embodiments 56-60, wherein the subject has received a prior treatment for diabetic retinopathy.

Embodiment 62. The method of Embodiment 61, wherein the subject failed to respond to the prior treatment for diabetic retinopathy.

Embodiment 63. The method of Embodiment 61 or 62, wherein the prior treatment was therapeutic procedure selected from a vitrectomy and laser surgery, or a therapeutic agent selected from a steroid and an anti-vascular endothelial growth factor (VEGF) therapy.

Embodiment 64. The method of Embodiment 63, wherein the anti-VEGF therapy is an anti-VEGF antibody selected from the group consisting of bevacizumab, ranibizumab, and aflibercept.

Embodiment 65. The method of any one of Embodiments 56-64, wherein the anti-ceramide antibody or antigen-binding fragment thereof is administered as a single dose.

Embodiment 66. The method of any one of Embodiments 56-64, wherein the anti-ceramide antibody or antigen-binding fragment thereof is administered in two or more doses separated by at least two weeks, at least three weeks, or at least four weeks.

Embodiment 67. The method of any one of Embodiments 56-64, wherein the anti-ceramide antibody or antigen-binding fragment thereof is administered in two or more doses separated by about two weeks to about four weeks.

Embodiment 68. The method of any one of Embodiments 56-64, wherein the anti-ceramide antibody or antigen-binding fragment thereof is administered in two or more doses separated by at least one month, at least two months, at least three months, at least four months, at least five months, at least six months, at least seven months, at least eight months, at least nine months, at least ten months, or at least eleven months.

Embodiment 69. The method of any one of Embodiments 56-64, wherein the anti-ceramide antibody or antigen-binding fragment thereof is administered in two or more doses separated by about one month to about six months.

Embodiment 70. The method of any one of Embodiments 56-64, wherein the anti-ceramide antibody or antigen-binding fragment thereof is administered in two or more doses separated by at least one year.

Embodiment 71. The method of any one of Embodiments 56-70, wherein the anti-ceramide antibody or antigen-binding fragment thereof is administered before the onset of one or more symptoms of the ocular inflammatory disease.

Embodiment 72. The method of any one of Embodiments 56-70, wherein the anti-ceramide antibody or antigen-binding fragment thereof is administered after the onset of one or more symptoms of the ocular inflammatory disease.

Embodiment 73. The method of any one of Embodiments 1-72, wherein the anti-ceramide antibody or antigen-binding fragment thereof comprises a variable heavy chain ($V_H$) and a variable light chain ($V_L$), wherein the $V_H$ comprises a heavy chain complementarity determining region 1 (HCDR1) comprising the amino acid sequence of GYTFTDHTIH (SEQ ID NO: 1), an HCDR2 comprising the amino acid sequence of YNYPRDGSTKYNEKFKG (SEQ ID NO: 2), and an HCDR3 comprising the amino acid sequence of GFITTVVPSAY (SEQ ID NO: 3), and wherein the $V_L$ comprises a light chain complementarity determining region 1 (LCDR1) comprising the amino acid sequence of RASKSISKYLA (SEQ ID NO: 4), an LCDR2 comprising the amino acid sequence of SGSTLQS (SEQ ID NO: 5), and an LCDR3 comprising the amino acid sequence of QQHNEYPWT (SEQ ID NO: 6).

Embodiment 74. The method of any one of Embodiments 1-72, wherein the $V_H$ comprises the amino acid sequence of SEQ ID NO: 7 and wherein the $V_L$ comprises the amino acid sequence of SEQ ID NO: 8.

Embodiment 75. The method of any one of Embodiments 1-74, wherein the anti-ceramide antibody or antigen-binding fragment thereof is a 6B5 antibody.

Embodiment 76. The method of any one of Embodiments 1-74, wherein the anti-ceramide antibody or antigen-binding fragment thereof is a 6B5 scFv.

Embodiment 77. The method of any one of Embodiments 1-72, wherein the anti-ceramide antibody or antigen-binding fragment thereof comprises a variable heavy chain ($V_H$) and a variable light chain ($V_L$), wherein the $V_H$ comprises a heavy chain complementarity determining region 1 (HCDR1) comprising the amino acid sequence of NYWMH (SEQ ID NO: 33), an HCDR2 comprising the amino acid sequence of AIYPGDSDTSYNQKFKG (SEQ ID NO: 34), and an HCDR3 comprising the amino acid sequence of LYYGYD (SEQ ID NO: 35), and wherein the $V_L$ comprises a light chain complementarity determining region 1 (LCDR1) comprising the amino acid sequence of KSSQSLIDSDGKTFLN (SEQ ID NO: 36), an LCDR2 comprising the amino acid sequence of LVSKLDS (SEQ ID NO: 37), and an LCDR3 comprising the amino acid sequence of WQGTHFPYT (SEQ ID NO: 38).

Embodiment 78. The method of any one of Embodiments 1-72, wherein the $V_H$ comprises the amino acid sequence of SEQ ID NO: 39 and wherein the $V_L$ comprises the amino acid sequence of SEQ ID NO: 40.

Embodiment 79. The method of any one of Embodiments 1-72 and 77-78, wherein the anti-ceramide antibody or antigen-binding fragment thereof is a 2A2 antibody.

Embodiment 80. The method of any one of Embodiments 1-72 and 77-78, wherein the anti-ceramide antibody or antigen-binding fragment thereof is a 2A2 scFv.

Embodiment 81. The method of any one of the foregoing Embodiments, wherein preventing diabetic retinopathy or the ocular inflammatory disease comprises delaying the onset of diabetic retinopathy or the ocular inflammatory disease.

Embodiment 82. The method of any one of the foregoing Embodiments, wherein one or more symptoms of diabetic retinopathy or the ocular inflammatory disease are reduced in the subject compared to a control subject or compared to the subject prior to treatment with the anti-ceramide antibody or antigen-binding fragment thereof.

Embodiment 83. The method of Embodiment 82, wherein the one or more symptoms of diabetic retinopathy or the ocular inflammatory disease are selected from retinal inflammation, acellular capillary formation, retinal neovascularization, retinal endothelial cell death, retinal vascular permeability, retinal ischemia-reperfusion injury, retinal leakage area, and occludin disruption.

Embodiment 84. The method of Embodiment 82 or 83, wherein the one or more symptoms of diabetic retinopathy or the ocular inflammatory disease are reduced by at least 10%, at least 20%, at least 30%, at least 40%, or at least 50% compared to the control subject or compared to the subject prior to treatment with the anti-ceramide antibody or antigen-binding fragment thereof.

Embodiment 85. The method of any one of the foregoing Embodiments, wherein the expression level of one or more inflammatory markers in the eye is reduced compared to the expression level in the eye of a control subject or compared to the expression level in the subject's eye prior to treatment with the anti-ceramide antibody or antigen-binding fragment thereof.

Embodiment 86. The method of Embodiment 85, wherein the one or more inflammatory markers is selected from a cytokine, a growth factor, and an adhesion molecule.

Embodiment 87. The method of Embodiment 86, wherein the cytokine is selected from TNFα, IL-1β, IL-6, or MCP1.

Embodiment 88. The method of Embodiment 86, wherein the growth factor is VEGF.

Embodiment 89. The method of Embodiment 86, wherein the adhesion molecule is ICAM-1 or VCAM-1.

Embodiment 90. The method of any one of Embodiments 85-89, wherein the expression level of the one or more inflammatory markers in the subject's eye is decreased by at least 10%, at least 20%, at least 30%, at least 40%, or at least 50% compared to the expression level in the eye of a control subject or compared to the expression level in the subject's eye prior to treatment with the anti-ceramide antibody or antigen-binding fragment thereof.

Embodiment 91. The method of any one of the foregoing Embodiments, wherein one or more vision parameters are increased in the subject compared to the vision parameters a control subject or compared to the vision parameters of the subject prior to treatment with the anti-ceramide antibody or antigen-binding fragment thereof.

Embodiment 92. The method of Embodiment 91, wherein the one or more vision parameters are selected from peripheral vision; night vision; color vision; distance vision; close-range vision; and vision clarity.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. A method of treating or preventing diabetic retinopathy in a subject in need thereof comprising ocularly administering an anti-ceramide antibody or antigen-binding fragment thereof to the subject,
wherein the anti-ceramide antibody or antigen-binding fragment thereof comprises a variable heavy chain (VH) and a variable light chain (VL),
wherein the VH comprises a heavy chain complementarity determining region 1 (HCDR1) comprising the amino acid sequence of NYWMH (SEQ ID NO: 33), an HCDR2 comprising the amino acid sequence of AIYPGDSDTSYNQKFKG (SEQ ID NO: 34), and an HCDR3 comprising the amino acid sequence of LYYGYD (SEQ ID NO: 35), and
wherein the VL comprises a light chain complementarity determining region 1 (LCDR1) comprising the amino acid sequence of KSSQSLIDSDGKTFLN (SEQ ID NO: 36), an LCDR2 comprising the amino acid sequence of LVSKLDS (SEQ ID NO: 37), and an LCDR3 comprising the amino acid sequence of WQGTHFPYT (SEQ ID NO: 38).

2. The method of claim 1, wherein the anti-ceramide antibody or antigen-binding fragment thereof is a single-chain variable fragment (scFv).

3. The method of claim 1, wherein the administration is intravitreal administration.

4. The method of claim 1, wherein the anti-ceramide antibody or antigen-binding fragment thereof is administered as a single dose.

5. The method of claim 1, wherein the anti-ceramide antibody or antigen-binding fragment thereof is administered before or after the onset of one or more symptoms of diabetic retinopathy.

6. The method of claim 1, wherein the VH comprises the amino acid sequence of SEQ ID NO: 41 and wherein the VL comprises the amino acid sequence of SEQ ID NO: 42.

7. The method of claim 1, wherein the anti-ceramide antibody or antigen-binding fragment thereof is a 2A2 antibody or a 2A2 scFv.

8. The method of claim 1, wherein preventing diabetic retinopathy comprises delaying the onset of diabetic retinopathy.

9. The method of claim 1, wherein one or more symptoms of diabetic retinopathy are reduced in the subject compared to a control subject or compared to the subject prior to treatment with the anti-ceramide antibody or antigen-binding fragment thereof.

10. The method of claim 9, wherein the one or more symptoms of diabetic retinopathy are selected from retinal inflammation, acellular capillary formation, retinal neovascularization, retinal endothelial cell death, retinal vascular permeability, retinal ischemia-reperfusion injury, retinal leakage area, and occludin disruption.

11. The method of claim 9, wherein the one or more symptoms of diabetic retinopathy or the ocular inflammatory disease are reduced by at least 10%, at least 20%, at least 30%, at least 40%, or at least 50% compared to the control subject or compared to the subject prior to treatment with the anti-ceramide antibody or antigen-binding fragment thereof.

12. The method of claim 1, wherein the expression level of one or more inflammatory markers in the eye is reduced compared to the expression level in the eye of a control subject or compared to the expression level in the subject's eye prior to treatment with the anti-ceramide antibody or antigen-binding fragment thereof.

13. The method of claim 12, wherein the expression level of the one or more inflammatory markers in the subject's eye is decreased by at least 10%, at least 20%, at least 30%, at least 40%, or at least 50% compared to the expression level in the eye of a control subject or compared to the expression level in the subject's eye prior to treatment with the anti-ceramide antibody or antigen binding fragment thereof.

14. The method of claim 12, wherein the one or more inflammatory markers is selected from a cytokine, a growth factor, and an adhesion molecule.

15. The method of claim 14, wherein the cytokine is selected from TNFα, IL-1β, IL-6, or MCP-1.

16. The method of claim 14, wherein the growth factor is VEGF.

17. The method of claim 14, wherein the adhesion molecule is ICAM-1 or VCAM-1.

18. The method of claim 1, wherein one or more vision parameters are increased in the subject compared to the vision parameters a control subject or compared to the vision parameters of the subject prior to treatment with the anti-ceramide antibody or antigen-binding fragment thereof.

19. The method of claim 18, wherein the one or more vision parameters are selected from peripheral vision; night vision; color vision; distance vision; close-range vision; and vision clarity.

* * * * *